United States Patent
Braunsmann et al.

(10) Patent No.: US 10,201,806 B2
(45) Date of Patent: Feb. 12, 2019

(54) CATALYST AND PROCESS FOR THE CONVERSION OF OXYGENATES TO OLEFINS

(71) Applicant: BASF SE, Ludwigshafen (DE)

(72) Inventors: Kirsten Braunsmann, Ludwigshafen (DE); Bernd Bastian Schaack, Bensheim (DE); Ekkehard Schwab, Neustadt (DE); Manuela Gaab, Heidelberg (DE); Mathias Feyen, Laudenbach (DE)

(73) Assignee: BASF SE, Ludwigshafen Am Rhein (DE)

( * ) Notice: Subject to any disclaimer, the term of this patent is extended or adjusted under 35 U.S.C. 154(b) by 36 days.

(21) Appl. No.: 15/105,611

(22) PCT Filed: Dec. 18, 2014

(86) PCT No.: PCT/EP2014/078514
§ 371 (c)(1),
(2) Date: Jun. 17, 2016

(87) PCT Pub. No.: WO2015/091832
PCT Pub. Date: Jun. 25, 2015

(65) Prior Publication Data
US 2016/0310934 A1    Oct. 27, 2016

(30) Foreign Application Priority Data

Dec. 20, 2013 (EP) ..................... 13199062

(51) Int. Cl.
| | | |
|---|---|---|
| *B01J 29/06* | (2006.01) | |
| *C07C 1/20* | (2006.01) | |
| *B01J 29/40* | (2006.01) | |
| *B01J 37/00* | (2006.01) | |
| *B01J 35/00* | (2006.01) | |
| *C07C 11/06* | (2006.01) | |
| *C07C 11/02* | (2006.01) | |
| *C07C 1/207* | (2006.01) | |
| *C07C 11/08* | (2006.01) | |
| *B01J 37/28* | (2006.01) | |
| *B01J 29/70* | (2006.01) | |

(Continued)

(52) U.S. Cl.
CPC ............ *B01J 29/40* (2013.01); *B01J 29/70* (2013.01); *B01J 29/7038* (2013.01); *B01J 35/002* (2013.01); *B01J 35/023* (2013.01); *B01J 35/10* (2013.01); *B01J 37/0009* (2013.01); *B01J 37/0201* (2013.01); *B01J 37/0236* (2013.01); *B01J 37/04* (2013.01); *B01J 37/08* (2013.01); *B01J 37/28* (2013.01); *C07C 1/20* (2013.01); *C07C 1/207* (2013.01); *C07C 11/02* (2013.01); *C07C 11/06* (2013.01); *C07C 11/08* (2013.01); *B01J 29/90* (2013.01); *B01J 37/0018* (2013.01); *B01J 37/0045* (2013.01); *B01J 38/02* (2013.01); *B01J 2229/12* (2013.01); *B01J 2229/123* (2013.01); *B01J 2229/186* (2013.01); *B01J 2229/20* (2013.01); *B01J 2229/32* (2013.01); *B01J 2229/37* (2013.01); *B01J 2229/42* (2013.01); *C07C 2529/40* (2013.01); *C07C 2529/70* (2013.01); *Y02P 20/584* (2015.11)

(58) Field of Classification Search
CPC ........ B01J 29/40; B01J 29/70; B01J 29/7038; B01J 2229/32; B01J 2229/37; B01J 2229/42; B01J 2229/123; B01J 2229/186; B01J 2229/20; B01J 2229/18; B01J 2229/12; B01J 35/10; B01J 35/002; B01J 37/0201; B01J 37/0236; B01J 37/08; B01J 37/04; B01J 37/0018; B01J 37/0045; B01J 37/0009; B01J 37/28; C07C 2529/40; C07C 2529/70; C07C 1/20; C07C 1/207; C07C 11/06; C07C 11/02; C07C 11/08
USPC ............ 502/60, 63, 64, 67, 71, 77; 585/638, 585/639, 640
See application file for complete search history.

(56) References Cited

U.S. PATENT DOCUMENTS

| | | |
|---|---|---|
| 4,049,573 A | 9/1977 | Kaeding |
| 4,504,690 A | 3/1985 | Forbus et al. |

(Continued)

FOREIGN PATENT DOCUMENTS

| | | |
|---|---|---|
| CN | 102049302 A | 5/2011 |
| CN | 102049313 A | 5/2011 |

(Continued)

OTHER PUBLICATIONS

Ciambelli, P., et al., "Acid-base catalysis in the conversion of methanol to olefins over Mg-modified ZSM-5 zeolite", Successful Design of Catalysts, 1988, pp. 239-246.

(Continued)

*Primary Examiner* — Elizabeth D Wood
(74) *Attorney, Agent, or Firm* — Drinker Biddle & Reath LLP

(57) ABSTRACT

The present invention relates to a catalyst for the conversion of oxygenates to olefins, wherein the catalyst comprises one or more zeolites of the MFI, MEL and/or MWW structure type and particles of one or more metal oxides, the one or more zeolites of the MFI, MEL and/or MWW structure type comprising one or more alkaline earth metals selected from the group consisting of Mg, Ca, Sr, Ba and combinations of two or more thereof, wherein the catalyst displays a water uptake of 9.0 wt.-% or less, as well as to a process for the production thereof and to its use, in particular in a process for converting oxygenates to olefins.

33 Claims, No Drawings

(51) Int. Cl.
- *B01J 35/02* (2006.01)
- *B01J 35/10* (2006.01)
- *B01J 37/02* (2006.01)
- *B01J 37/04* (2006.01)
- *B01J 37/08* (2006.01)
- *B01J 38/02* (2006.01)
- *B01J 29/90* (2006.01)

(56) References Cited

U.S. PATENT DOCUMENTS

| | | | |
|---|---|---|---|
| 5,013,700 A * | 5/1991 | Falth | B01J 20/186 502/64 |
| 6,051,519 A | 4/2000 | Wu et al. | |
| 2014/0058180 A1 | 2/2014 | Klingelhöfer et al. | |

FOREIGN PATENT DOCUMENTS

| | | |
|---|---|---|
| DE | 238733 A1 | 9/1986 |
| JP | 2012087079 A | 5/2012 |
| WO | WO-2011089263 A1 | 7/2011 |
| WO | WO-2012123556 A1 | 9/2012 |
| WO | WO-2012123557 A1 | 9/2012 |
| WO | WO-2012123558 A1 | 9/2012 |
| WO | WO-2012/152406 A1 | 11/2012 |

OTHER PUBLICATIONS

Freiding, J., et al., "Extrusion of zeolites: Properties of catalysts with a novel aluminium phosphate sintermatrix", Applied Catalysis A: General, 2007, vol. 328, pp. 210-218.

Goryainova, T., et al., "Study of Magnesium-Containing Zeolite Catalysts for the Synthesis of Lower Olefins from Dimethyl Ether", Petroleum Chemistry, 2011, vol. 51, No. 3, pp. 169-173.

Le Van Mao, R., et al., "Composite ZSM-5 zeolite/asbestos catalysts", 1985, vol. 63, No. 12, pp. 3464-3470.

Lee Y., et al., "Novel aluminophosphate (AIPO) bound ZSM-5 extrudates with improved catalytic properties for methanol to propylene (MTP) reaction", Applied Catalysis A: General, 2010, vol. 374, pp. 18-25.

McIntosh R., et al., The Properties of Magnesium and Zinc Oxide Treated ZSM-5 Catalysts for Conversion of Methanol Into Olefin-Rich Products, Applied Catalysis, 1983, vol. 6, pp. 307-314.

Okado, H., et al., "Deactivation Resistance of ZSM-5-Type Zeolites containing Alkaline Earth Metals used for Methanol Conversion", Applied Catalysis, 1988, vol. 41, pp. 121-135.

Zhao Y., et al., "Effect of metal modification of HZSM-5 on catalyst stability in the shape-selective methylation of toluene", Catalysis Today, 2010, vol. 156, pp. 69-73.

Zhao, Y., et al., "Effect of Pt on stability of nano-scale ZSM-5 catalyst for toluene alkylation with methanol into p-xylene", Catalysis Today, 2011, vol. 160, pp. 179-183.

International Search Report with Written Opinion of the International Searching Authority for PCT/EP2014/078514 dated Mar. 16, 2015.

* cited by examiner

CATALYST AND PROCESS FOR THE CONVERSION OF OXYGENATES TO OLEFINS

CROSS-REFERENCE TO RELATED APPLICATIONS

This application is a national stage application (under 35 U.S.C. § 371) of PCT/EP2014/078514, filed Dec. 18, 2014, which claims benefit of European Application No. 13199062.4, filed Dec. 20, 2013, both of which are incorporated herein by reference in their entirety.

The present invention relates to a catalyst for the conversion of oxygenates to olefins, and to a process for the preparation thereof. The present invention further relates to a process for the conversion of oxygenates to olefins, and to the use of a catalyst according to the present invention in specific catalytic processes.

INTRODUCTION

In view of increasing scarcity of mineral oil deposits which serve as starting material for preparation of lower hydrocarbons and derivatives thereof, alternative processes for preparing such commodity chemicals are becoming increasingly important. In alternative processes for obtaining lower hydrocarbons and derivatives thereof, specific catalysts are frequently used in order to obtain lower hydrocarbons and derivatives thereof, such as unsaturated lower hydrocarbons in particular, with maximum selectivity from other raw materials and/or chemicals. In this context, important processes include those in which methanol as a starting chemical is subjected to a catalytic conversion, which can generally give rise to a mixture of hydrocarbons and derivatives thereof, and also aromatics.

In the case of such catalytic conversions, it is a particular challenge to refine the catalysts used therein, and also the process regime and parameters thereof, in such a way that a few very specific products form with maximum selectivity in the catalytic conversion. Thus, these processes are named particularly according to the products which are obtained in the main therein. In the past few decades, particular significance has been gained by those processes which enable the conversion of methanol to olefins and are accordingly characterized as methanol-to-olefin processes (MTO process for methanol to olefins). For this purpose, there has been development particularly of catalysts and processes which convert methanol via the dimethyl ether intermediate to mixtures whose main constituents are ethene and propene.

DD 238733 A1 relates, for example, to a magnesium-doped zeolite and to the use thereof in the conversion of methanol to lower olefins, specifically of the carbon number range ≥3. McIntosh et al. in Applied Catalysis 1983, 6, p. 307-314 describes specifically ZSM-5 catalysts and the use thereof in methanol-to-olefin processes, and the doping thereof with various metals and nonmetals, for example magnesium or phosphorus, and the influence thereof on the yields and product distribution in the catalytic conversion of methanol.

Lee et al. in Applied Catalysis A 2010, 374, p. 18-25 relates to ZSM-5 extrudates with aluminophosphate binder and to the use thereof in methanol-to-propylene processes (MTP processes). Freiding et al. in Applied Catalysis A 2007, 328, p. 210-218 describes extrudates of ZSM-5 in an aluminophosphate sinter matrix.

U.S. Pat. No. 4,049,573 relates to a catalytic process for conversion of lower alcohols and ethers thereof, and especially methanol and dimethyl ether, selectively to a hydrocarbon mixture with a high proportion of C2-C3 olefins and monocyclic aromatics and especially para-xylene, the catalysts used therein being doped with boron, magnesium and/or phosphorus.

Goryainova et al. in Petroleum Chemistry 2011, vol. 51, no. 3, p. 169-173 describes the catalytic conversion of dimethyl ether to lower olefins using magnesium-containing zeolites.

Ciambelli et al. "Acid-base catalysis in the conversion of methanol to olefins over Mg-modified ZSM-5 zeolite", Successful Design of Catalysts, Elsevier Science Publishers B.V., Amsterdam, 1988, p. 239-246 examines the influence of magnesium in the MTO process and especially in combination with ZSM-5 zeolite as a catalyst.

Okado et al. in Applied Catalysis 1988, 41, p. 121-135 relates to methanol-to-olefin processes using the ZSM-5 catalyst and examines the influence of various alkaline earth metals with regard to deactivation of the catalyst during the service life thereof.

WO 2012/123556 A1 relates to a catalyst which is produced by mixing a zeolite of the pentasil type which has been modified by a first phosphorus compound with alumina and an acid and processing the mixture to give a shaped body, which is then impregnated with a second phosphorus compound. WO 2012/123558 A1 describes a catalyst which is produced by impregnating a zeolite-containing shaped body with a phosphorus compound, the zeolite being of the pentasil type. Finally, WO 2012/123557 A1 relates to a catalyst which is prepared by mixing a zeolite of the pentasil type, which has first been modified by a phosphorus compound which is then substantially removed again from the zeolite, with alumina and an acid, and processing the mixture to give a shaped body.

CN 102049302 A relates to a method for the preparation of a catalyst involving an acid treatment and a surface silanazation treatment of an aluminosilicate molecular sieve, wherein the catalyst is employed for converting methanol and dimethylether selectively to gasoline components. CN 102049313 A, on the other hand, concerns a method for the preparation of a catalyst involving the loading of an aluminosilicate molecular sieve with metal ions and then carrying out a silanization treatment, wherein the catalyst may be employed for the conversion of methanol to olefins. JP 2012-087079 A relates to a method for converting ethanol to lower olefins which employs a ZSM-5 zeolite catalyst which has been treated with an alkoxysilane compound. U.S. Pat. No. 6,051,519 concerns a catalyst composition comprising a silylated zeolite and a promoter comprising a Group VIII metal, wherein the catalyst composition may be used for the isomerization of ethylbenzene. Finally, WO 2012/152406 A1 relates to an aluminosilicate zeolite which has been surface treated with an organic silicon compound and to its use as a catalyst for the alkylation of aromatic hydrocarbons.

WO 2011/089263 A1 relates to a method for making a catalyst comprising a phosphorus modified zeolite which may be used in an alcohol dehydration process. U.S. Pat. No. 4,504,690 A concerns an organophosphorus-treated zeolite catalyst for para-selective conversion of aromatics. Zhao et al. in Catalysis Today 2011, 160, pp. 179-183 deals with the effect of Pt on the stability of a nano-scale ZSM-5 catalyst for the alkylation of toluene with methanol to p-xylene. Zhao et al. in Catalysis Today 2010, 156, pp. 69-73 relates to the effect of the metal modification of HZSM-5 on the stability of the catalyst in the shape-selective methylation of toluene. Finally, Le Van Mao et al. in Can. J. Chem. 1985, 63, pp. 3464-3470 concerns a composite ZSM-5 zeolite/asbestos catalyst.

In spite of the advances which have been achieved with respect to the selectivities of different catalysts in processes for preparing lower hydrocarbons and derivatives thereof, this covers only a portion of the possible products. Thus, there is still a need for new processes and catalysts which can have high selectivities with respect to particular products and product mixtures, especially with respect to the olefins of different chain length which are obtained in such processes. Irrespective of this, there is still a general need for new catalysts and processes which, in addition to having new and/or improved selectivities, also have better resistance to any deactivation in such processes, especially as a result of coking of the catalyst, in order thus to be able to enable a higher efficiency of existing and new processes.

DETAILED DESCRIPTION

It was thus an object of the present invention to provide an improved catalyst, especially for the conversion of oxygenates to olefins, which has new and improved selectivities with respect to particular process products. More particularly, it was an object of the present invention to provide improved catalysts and processes for the conversion of oxygenates to olefins, which exhibit a specific selectivity with respect to C3 and C4 olefins. It was an additional object of the present invention to provide catalysts and processes which enable a longer service life of the catalyst with comparable space velocity and conversion of oxygenates. It was a further object of the present invention to provide an improved catalyst which produces a lower level of unwanted by-products, and especially an improved catalyst and a process for the conversion of oxygenates to olefins using the latter, which produces a smaller amount of lightweight gases such as methane, ethane and propane, and especially a smaller amount of methane, as an unwanted by-product of the reaction.

It has thus been found that, surprisingly, a catalyst for the conversion of oxygenates to olefins, which contains a metal oxide in addition to a zeolite of the MFI, MEL and/or MWW structure type comprising one or more alkaline earth metals and which is optionally doped with phosphorous, wherein said catalyst displays a particularly low water uptake not only exhibits a surprisingly high selectivity with respect to C3 and C4 olefins, but unexpectedly also possesses a considerably improved service life. More particularly, it has been found that, unexpectedly, a synergistic effect of the doping of one or more zeolites with one or more alkaline earth metals in combination with a low water uptake, i.e. a high hydrophobicity, of the catalyst can be achieved, both with respect to the olefin selectivity in the case of use of the catalyst for conversion of oxygenates as well as and in particular with respect to a considerable improvement in the resistance of the catalyst to deactivation during the use thereof in a catalytic process.

Thus, the present invention relates to a catalyst for the conversion of oxygenates to olefins, wherein the catalyst comprises one or more zeolites of the MFI, MEL and/or MWW structure type and particles of one or more metal oxides, the one or more zeolites of the MFI, MEL and/or MWW structure type comprising one or more alkaline earth metals selected from the group consisting of Mg, Ca, Sr, Ba and combinations of two or more thereof, wherein the catalyst displays a water uptake of 9.0 wt.-% or less, preferably of 8.0 wt.-% or less, more preferably of 7.0 wt.-% or less, more preferably of 6.0 wt.-% or less, more preferably of 5.5 wt.-% or less, wherein more preferably the catalyst displays a water uptake ranging from 0.5 to 5.0 wt.-%, more preferably of 1.0 to 4.5 wt.-%, more preferably of 1.5 to 4.0 wt.-%, more preferably of 2.0 to 3.5 wt.-%, and more preferably of 2.5 to 3.0 wt.-%.

With regard to the one or more zeolites present in the catalyst, according to the present invention, there are no restrictions whatsoever either with respect to the type or with respect to the number of zeolites which can be used herein, provided that they are zeolites of one or more of the MFI, MEL and MWW structure types. If one or more of the zeolites present in the catalyst are of the MWW structure type, there is again no restriction whatsoever with respect to the type and/or number of MWW zeolites which can be used according to the present invention. Thus, these may be selected, for example, from the group of zeolites of the MWW structure type consisting of MCM-22, [Ga—Si—O]-MWW, [Ti—Si—O]-MWW, ERB-1, ITQ-1, PSH-3, SSZ-25 and mixtures of two or more thereof, preference being given to the use of zeolites of the MWW structure type which are suitable for the conversion of oxygenates to olefins, especially MCM-22 and/or MCM-36.

The same applies correspondingly to the zeolites of the MEL structure type which can be used according to the present invention in the catalyst, these being selected, for example, from the group consisting of ZSM-11, [Si—B—O]-MEL, boron-D (MFI/MEL mixed crystal), boralite D, SSZ-46, silicalite 2, TS-2 and mixtures of two or more thereof. Here too, preference is given to using those zeolites of the MEL structure type which are suitable for the conversion of oxygenates to olefins, especially [Si—B—O]-MEL.

According to the present invention, however, especially zeolites of the MFI structure type are used in the inventive catalyst for the conversion of oxygenates to olefins. With regard to these preferred embodiments of the present invention, there is likewise no restriction whatsoever with respect to the type and/or number of the zeolites of this structure type used, the one or more zeolites of the MFI structure type which are used in the inventive catalyst preferably being selected from the group consisting of ZSM-5, ZBM-10, [As—Si—O]-MFI, [Fe—Si—O]-MFI, [Ga—Si—O]-MFI, AMS-1B, AZ-1, boron-C, boralite C, encilite, FZ-1, LZ-105, monoclinic H-ZSM-5, mutinaite, NU-4, NU-5, silicalite, TS-1, TSZ, TSZ-III, TZ-01, USC-4, USI-108, ZBH, ZKQ-1B, ZMQ-TB and mixtures of two or more thereof. Further preferably, according to the present invention, the catalyst comprises ZSM-5 and/or ZBM-10 as the zeolite of the MFI structure type, particular preference being given to using ZSM-5 as the zeolite. With regard to the zeolitic material ZBM-10 and the preparation thereof, reference is made, for example, to EP 0 007 081 A1 and to EP 0 034 727 A2, the content of which, particularly with regard to the preparation and characterization of the material, is hereby incorporated into the present invention.

Thus, according to the present invention, it is preferred that the catalyst for the conversion of oxygenates to olefins comprises one or more zeolites of the MFI structure type, and more preferably one or more zeolites of the MFI structure type selected from the group consisting of ZSM-5, ZBM-10, [As—Si—O]-MFI, [Fe—Si—O]-MFI, [Ga—Si—O]-MFI, AMS-1B, AZ-1, boron-C, boralite C, encilite, FZ-1, LZ-105, monoclinic H-ZSM-5, mutinaite, NU-4, NU-5, silicalite, TS-1, TSZ, TSZ-III, TZ-01, USC-4, USI-108, ZBH, ZKQ-1B, ZMQ-TB and mixtures of two or more thereof, further preferably from the group consisting of ZSM-5, ZBM-10 and mixtures thereof, the zeolite of the MFI structure type preferably being ZSM-5.

According to the present invention, it is preferred that the catalyst does not comprise any significant amounts of one or more nonzeolitic materials and especially does not comprise any significant amounts of one or more aluminophosphates (AlPOs or APOs) or of one or more aluminosilicophosphates (SAPOs). In the context of the present invention, the catalyst is essentially free of or does not comprise any significant amounts of a specific material in cases in which this specific material is present in the catalyst in an amount of % by weight or less based on 100% by weight of the total amount of the one or more zeolites of the MFI, MEL and/or MWW structure type, preferably in an amount of 0.5% by weight or less, further preferably of 0.1% by weight or less, further preferably of 0.05% by weight or less, further preferably of 0.001% by weight or less, further preferably of 0.0005% by weight or less and further preferably in an amount of 0.0001% by weight or less. A specific material in the context of the present invention particularly denotes a particular element or a particular combination of elements, a particular substance or a particular substance mixture, and also combinations and/or mixtures of two or more thereof.

The aluminophosphates (AlPOs and APOs) in the context of the present invention generally include all crystalline aluminophosphate phases. According to a preferred definition of the aluminophosphates (AlPOs and APOs), these include the materials AlPO-20 and composition variants thereof, AlPO-5, AlPO-21, AlPO-H3, AlPO-17 and composition variants thereof, AlPO-12-TAMU, AlPO-11, AlPO-22, AlPO-8, AlPO-C, AlPO-25, AlPO-16, AlPO-31, AlPO-8, AlPO-H2, AlPO-31, AlP-34, AlPO-D, AlPO-18, AlPO-EN3, AlPO-53(A), AlPO-41, AlPO-52, AlPO4-pollucite, AlPO-24, AlPO-C, AlP-33, AlPO-17 and composition variants thereof, AlPO-20 and composition variants thereof, AlPO-H2, AlP-14, AlPO-54, AlPO-53(B), AlPO-40, AlPO-35, AlPO-CJB1 (optionally with additional presence of phosphate groups), AlPO-40, AlPO-36, MnAPO-11, MAPO-43, CoAPO-5, MAPO-36, MgAPO-50, ZAPO-M1, GaPO-DAB-2, CrAPO-5, CoAPO-50, MAPO-39, CoAPO-44, GaPO-34, MeAPO-47, GaPO-DAB-2, CoAPO-47, MeAPO-47, GaPO-14, CoAPO-50, CFSAPO-1A, GeAPO-11, CoAPO-5, MAPO-5 (where M=Mg, Mn), VAPO-5, ZnAPO-5, FAPO-5, MnAPO-41, CoAPO-40, ZnAPO-40, MAPO-46, MnAPO-50, CoAPO-H3, ZnAPO-39, MAPO-31 (where M=Zn, Mg, Mn, Co, Cr, Cu, Cd), ZnAPO-36, ZnAPO-35, FAPO-H1, MnAPO-14, ZnAPO-50, APO-CJ3, FAPO-36, MAPO-31 (where M=Mn, Ni, Zn), VAPO-31, MAPO-5 (where M=Cd, Cu, Mo, V/Mo, Zr) and CoAPO-CJ40. According to a preferred definition of the aluminophosphates (AlPOs and APOs), these include all crystalline aluminophosphate phases which consist of aluminum, phosphorus and oxygen, and especially the materials AlPO-5, AlPO-21, AlPO-H3, AlPO-17 and composition variants thereof, AlPO-12-TAM, AlPO-11, AlPO-22, AlPO-8, AlPO-C, AlPO-25, AlPO-16, AlPO-31, AlPO-8, AlPO-H2, AlPO-31, AlPO-34, AlPO-D, AlPO-18, AlPO-EN3, AlPO-53(A), AlPO-41, AlPO-52, AlPO4-pollucite, AlLPO-24, AlPO-C, AlPO-33, AlPO-17 and composition variants thereof, AlPO-20 and composition variants thereof, AlPO-H2, AlPO-14, AlPO-54, AlPO-53(B), AlPO-40, AlPO-35, AlPO-CJB1 (optionally with additional presence of phosphate groups), AlPO-40 and AlPO-36.

The aluminosilicophosphates (SAPOs) in the context of the present invention generally include all crystalline aluminosilicophosphate phases, especially the SAPO materials SAPO-11, SAPO-47, SAPO-40, SAPO-43, SAPO-5, SAPO-31, SAPO-34, SAPO-37, SAPO-35, SAPO-42, SAPO-56, SAPO-18, SAPO-41, SAPO-39 and CFSAPO-1A.

According to the present invention, the one or more zeolites of the MFI, MEL and/or MWW structure type comprises one or more alkaline earth metals selected from the group consisting of Mg, Ca, Sr, Ba and combinations of two or more thereof. In general, according to the present invention, there is no restriction whatsoever either with regard to the type and/or the number of alkaline earth metals present in the one or more zeolites, or with regard to the manner in which they are present in the one or more zeolites, provided that the one or more zeolites comprise one or more alkaline earth metals selected from the group consisting of magnesium, calcium, strontium, barium and combinations of two or more thereof. According to the present invention, the one or more alkaline earth metals, however, are preferably selected from the group consisting of magnesium, calcium, strontium and combinations of two or more thereof, and, in particularly preferred embodiments of the inventive catalyst, the alkaline earth metal is magnesium. In alternatively preferred embodiments of the present invention, the catalyst does not comprise any, or any significant amounts of, calcium and/or strontium.

Thus, according to the present invention, it is preferred that the alkaline earth metals present in the one or more zeolites of the MFI, MEL and/or MWW structure type are selected from the group consisting of Mg, Ca, Sr and combinations of two or more thereof, the alkaline earth metal more preferably being Mg.

With regard to the manner in which the one or more alkaline earth metals are present in the one or more zeolites in the catalyst, these may in principle be present in the micropores of the one or more zeolites and/or as a constituent of the zeolitic framework, especially at least partly in isomorphic substitution for an element in the zeolite framework, preferably for silicon and/or aluminum as a constituent of the zeolite framework and more preferably at least partly in isomorphic substitution for aluminum. With regard to the presence of the one or more alkaline earth metals in the micropores of the one or more zeolites, these may be present as a separate compound, for example as a salt and/or oxide therein, and/or as a positive counterion to the zeolite framework. According to the present invention, the one or more alkaline earth metals are present at least partly in the pores and preferably in the micropores of the one or more zeolites, and, further preferably, the one or more alkaline earth metals are present therein at least partly as the counterion of the zeolite framework, as can arise, for example, in the course of production of the one or more zeolites in the presence of the one or more alkaline earth metals and/or can be brought about by performance of an ion exchange with the one or more alkaline earth metals in the zeolite already produced.

With regard to the amount of the one or more alkaline earth metals, as already noted above, there are no particular restrictions according to the present invention with respect to the amount in which they are present in the one or more zeolites. It is thus possible in principle for any possible amount of the one or more alkaline earth metals to be present in the one or more zeolites, for example in a total amount of the one or more alkaline earth metals of 0.1-20% by weight based on the total amount of the one or more zeolites. According to the present invention, however, it is preferred that the one or more alkaline earth metals are present in a total amount in the range of 0.5-15% by weight based on 100% by weight of the total amount of the one or more zeolites, further preferably of 1-10% by weight, further preferably of 2-7% by weight, further preferably of 3-5% by weight and further preferably of 3.5-4.5% by weight. In particularly preferred embodiments of the present invention, the one or more alkaline earth metals are present in a total amount in the range of 3.8-4.2% by weight in the one or more zeolites. For all of the above percentages by weight for alkaline earth metal in the one or more zeolites, these are calculated proceeding from the one or more alkaline earth metals as the metal.

Thus, according to the present invention, it is preferred that the one or more zeolites of the MFI, MEL and/or MWW structure type comprise the one or more alkaline earth metals in a total amount in the range from 0.1 to 20% by weight, preferably from 0.5 to 15% by weight, further preferably from 1 to 10% by weight, further preferably from 2 to 7% by weight, further preferably from 3 to 5% by weight, further preferably from 3.5 to 4.5% by weight, and further preferably in the range from 3.8 to 4.2% by weight, based in each case on the total amount of the one or more zeolites of the MFI, MEL and/or MWW structure type and calculated as the metal. According to the present invention it is however alternatively preferred that the MFI, MEL and/or MWW structure type comprise the one or more alkaline earth metals in a total amount in the range from 0.1 to 10% by weight, further preferably from 0.5 to 5% by weight, further preferably from 0.8 to 3% by weight, further preferably from 1 to 2.5% by weight, further preferably from 1.2 to 2.2% by weight, and further preferably in the range from 1.6 to 2.0% by weight, based in each case on the total amount of the one or more zeolites of the MFI, MEL and/or WAN structure type and calculated as the metal.

According to the present invention, the catalyst for the conversion of oxygenates to olefins comprises, as well as the above-described zeolites, especially according to the particular and preferred embodiments as described in the present application, further particles of one or more metal oxides. According to the present invention, there are no restrictions whatsoever either with respect to the type metal oxides which may be used in the catalyst, or with respect to the number of different metal oxides which may be present therein. According to the present invention, however, preference is given to metal oxides which are generally used in catalytic materials as inert materials and especially as support substances, preferably with a large BET surface area. According to the present invention, figures for surface areas of a material are preferably based on the BET (Brunauer-Emmett-Teller) surface area thereof, this preferably being determined to DIN 66131 by nitrogen absorption at 77 K.

With regard to the metal oxides which can be used in the present invention, there are no restrictions whatsoever. It is thus possible in principle to use any suitable metal oxide compound and mixtures of two or more metal oxide compounds. Preference is given to using metal oxides which are thermally stable in processes for the conversion of oxygenates to olefins, the metal oxides preferably serving as binders. Thus, the one or more metal oxides which are used in the catalyst are preferably selected from the group consisting of silica, alumina, titania, zirconia, aluminum-titanium mixed oxides, aluminum-zirconium mixed oxides, aluminum-lanthanum mixed oxides, aluminum-zirconium-lanthanum mixed oxides, titanium-zirconium mixed oxides and mixtures of two or more thereof. Further preferably, according to the present invention, the one or more metal oxides are selected from the group consisting of silica, alumina, aluminum-titanium mixed oxides, aluminum-zirconium mixed oxides, aluminum-lanthanum mixed oxides, aluminum-zirconium-lanthanum mixed oxides and mixtures of two or more thereof. According to the present invention, particular preference is given to using the metal oxide alumina as particles in the catalyst.

Furthermore, no particular restrictions exist relative to further elements and compounds which may be contained in the one or more metal oxides contained in the catalyst for the conversion of oxygenates to olefins according to the present invention. Thus, any suitable further elements or compounds may be contained in the one or more metal oxides, wherein it is preferred that the one or more metal oxides comprise phosphorus. As regards the form in which the phosphorus may be contained in the one or more metal oxides according to said preferred embodiments of the present invention, no particular restrictions apply, such that phosphorus may be contained in the elemental form and/or as a phosphorus-containing compound such as in the form of a phosphorus-containing salt or molecule. According to the present invention it is however particularly preferred that according to preferred embodiments of the present invention wherein phosphorus is contained in the one or more metal oxides, said phosphorus is present therein at least partly in oxidic form.

Thus, it is preferred according to the present invention that the one or more zeolites of the MFI, MEL and/or MWW structure type comprise phosphorus, the phosphorus being present at least partly in oxidic form.

According to the present invention, it is further preferred that the metal oxide is at least partly in amorphous form. In preferred embodiments of the present invention, according to which the metal oxide is used at least partly in crystalline form and wherein the metal oxide further comprises phosphorous, it is preferred that the phosphorus present in the metal oxide is not present therein as part of the crystal structure of the metal oxide and hence does not form an element or part of the crystal structure that would at least partly require crystallinity of the metal oxide. More particularly, according to the present invention, it has been found that, surprisingly, specifically in combination with one or more alkaline earth metal-comprising zeolites according to the present invention, the application of phosphorus to a metal oxide as an additive and/or binder in a process for the conversion of oxygenates to olefins not only effectively suppresses the formation of coke on the catalyst, as a result of which the service life can be considerably prolonged, but also, unexpectedly, considerably and sustainably reduces the formation of unwanted by-products and especially of methane.

As noted above, according to the present invention, it is preferred that the particles of the one or more metal oxides and especially of the one or more metal oxides according to the particular and preferred embodiment as described in the present application comprise phosphorus. With respect to the form in which the phosphorus is present in the particles of the one or more metal oxides according to said preferred embodiments, there is no particular restriction whatsoever, provided that at least a portion of the phosphorus is in oxidic form. According to the present invention, phosphorus is in oxidic form if it is in present in conjunction with oxygen, i.e. if at least a portion of the phosphorus is at least partly in a compound with oxygen, especially with covalent bonding of at least a portion of the phosphorus to the oxygen. According to the present invention, it is further preferred that the phosphorus which is at least partly in oxidic form comprises oxides of phosphorus and/or oxide derivatives of phosphorus. The oxides of phosphorus according to the present invention include especially phosphorus trioxide, diphosphorus tetroxide, phosphorus pentoxide and mixtures of two or more thereof. In addition, according to the present invention, it is preferred that the phosphorus and especially the phosphorus in oxidic form is at least partly in amorphous form, the phosphorus and especially the phosphorus in oxidic form further preferably being present essentially in amorphous form. According to the present invention, the phosphorus and especially the phosphorus in oxidic form is essentially in amorphous form when the proportion of phosphorus and especially of phosphorus in oxidic form which is present in crystalline form in the catalyst is 1% by weight or less based on 100% by weight of the total amount of the particles of the one or more metal oxides, the phosphorus being calculated as the element, preferably in an amount of 0.5% by weight or less, further preferably of 0.1% by weight or less, further preferably of 0.05% by weight or less, further preferably of 0.001% by weight or less, further preferably of 0.0005% by weight or less and further preferably in an amount of 0.0001% by weight or less.

With regard to the manner in which the phosphorus which is at least partly in oxidic form is preferably present in the one or more metal oxides of the catalyst, according to the present invention, there is no particular restriction whatsoever, neither with respect to the manner in which it is present, nor with respect to the amount of phosphorus present in the one or more metal oxides. With respect to the manner in which the phosphorus may be present, it may thus in principle be applied to the one or more metal oxides as the element and/or as one or more independent compounds and/or incorporated in the one or more metal oxides, for example in the form of a dopant of the one or more metal oxides, this especially comprising embodiments in which the phosphorus and the one or more metal oxides at least partly form mixed oxides and/or solid solutions. According to the present invention, the phosphorus is preferably applied partly in the form of one or more oxides and/or oxide derivatives to the one or more metal oxides in the particles, the one or more oxides and/or oxide derivatives of phosphorus further preferably originating from a treatment of the one or more metal oxides with one or more acids of phosphorus and/or with one or more of the salts thereof. The one or more acids of phosphorus preferably refer to one or more acids selected from the group consisting of phosphinic acid, phosphonic acid, phosphoric acid, peroxophosphoric acid, hypodiphosphonic acid, diphosphonic acid, hypodiphosphoric acid, diphosphoric acid, peroxodiphosphoric acid and mixtures of two or more thereof. Further preferably, the one or more phosphoric acids are selected from the group consisting of phosphonic acid, phosphoric acid, diphosphonic acid, diphosphoric acid and mixtures of two or more thereof, further preferably from the group consisting of phosphoric acid, diphosphoric acid and mixtures thereof, and, in particularly preferred embodiments of the present invention, the phosphorus present in the one or more metal oxides at least partly originates from a treatment of the one or more metal oxides with phosphoric acid and/or with one or more phosphate salts.

According to the present invention, it is further preferred that the one or more zeolites of the MFI, MEL and/or MWW structure type comprise phosphorus. This applies independently as to whether the one or more metal oxides comprise phosphorous, wherein it is particularly preferred according to the present invention that in the catalyst for the conversion of oxygenates to olefins both the one or more metal oxides and the one or more zeolites of the MFI, MEL and/or MWW structure type comprise phosphorous. With regard to the form in which the phosphorus is present in the one or more zeolites, the same applies as described in the present application with respect to phosphorus preferably present in the one or more metal oxides, especially with regard to the partial presence thereof in oxidic form. With respect to the manner in which the phosphorus is present in the one or more zeolites, according to the present invention, it is preferably present in the pores of the zeolite framework and especially in the micropores thereof, either as an independent phosphorus-comprising compound and/or as a counterion to the zeolite framework, the phosphorus more preferably being present at least partly as an independent compound in the pores of the zeolite framework.

Thus, according to the present invention, further preference is given to embodiments of the catalyst for the conversion of oxygenates to olefins in which the one or more zeolites of the MFI, MEL and/or MWW structure type comprise phosphorus, the phosphorus being at least partly in oxidic form.

With regard to the ratio in which the one or more zeolites of the MFI, MEL and/or MWW structure type on the one hand and the particles of one or more metal oxides on the other hand are present in the catalyst according to the present invention, there is no particular restriction in principle, the ratio preferably corresponding to one suitable for the use of the catalyst in at least one of the preferred inventive uses of the catalyst according to the particular and preferred uses as described in the present application, and especially a use for the conversion of oxygenates to olefins. Thus, the weight ratio of zeolite to metal oxide in the catalyst according to the present invention and especially according to the particular and preferred embodiments of the present invention may be in the range from 10:90 to 95:5. According to the present invention, the zeolite:metal oxide weight ratio, however, is preferably in the range from 20:80 to 90:10, further preferably in the range from 40:60 to 80:20, further preferably in the range from 45:55 to 70:30, and further preferably in the range from 50:50 to 75:25. In particularly preferred embodiments of the present invention, the zeolite:metal oxide weight ratio is in the range from 55:45 to 65:35. In the context of the present invention, the zeolite:metal oxide weight ratio indicates especially the weight ratio of the total weight of the one or all of the plurality of zeolites to the total weight of the particles of the one or all of the plurality of metal oxides.

Thus, according to the present invention, preference is given to embodiments of the catalyst for the conversion of oxygenates to olefins in which the zeolite:metal oxide weight ratio in the catalyst is in the range from 10:90 to 95:5, preferably in the range from 20:80 to 90:10, more preferably in the range from 40:60 to 80:20, more preferably in the range from 45:55 to 70:30, more preferably of from 50:50 to 75:25, and more preferably in the range from 55:45 to 65:35.

With regard to the amount of phosphorus which may be preferably present in the catalyst according to the present invention, there is no restriction whatsoever in principle, and so all conceivably possible phosphorus contents may be present in the catalyst, these preferably being selected such that the catalyst can be used in at least one of the particular or preferred catalytic uses as described in the present application and especially for the conversion of oxygenates to olefins. Thus, the total amount of phosphorus in the catalyst according to the present invention may, for example, be in the range of 0.1-20% by weight, the total amount of phosphorus being based on the sum of the total weight of zeolites of the MFI, MEL and/or MWW structure type and the total weight of the particles of the one or more metal oxides, the phosphorus being calculated as the element. According to the present invention, the total amount of phosphorus in the catalyst, however, is preferably in the range of 0.5-15% by weight, further preferably in the range of 1-10% by weight, further preferably of 2-7% by weight, further preferably of 2.5-5% by weight, further preferably of 3.5-4.5% by weight, further preferably of 3.3-4.2% by weight and further preferably of 3.5-4% by weight. In particularly preferred embodiments of the present invention, the total amount of phosphorus in the catalyst based on the sum of the total weight of zeolites and the total weight of the particles of the one or more metal oxides is in the range of 3.6-3.8% by weight, the phosphorus being calculated as the element.

Thus, according to the present invention, it is preferred that the total amount of phosphorus in the catalyst for the conversion of oxygenates to olefins, based on the sum of the total weight of zeolites of the MFI, MEL and/or MWW structure type and the total weight of the particles of the one or more metal oxides and calculated as the element, is in the range from 0.1 to 20% by weight, preferably from 0.5 to 15% by weight, further preferably from 1 to 10% by weight, further preferably from 2 to 7% by weight, further preferably from 2.5 to 5% by weight, further preferably from 3 to 4.5% by weight, further preferably from 3.3 to 4.2% by weight, further preferably from 3.5 to 4% by weight, and further preferably in the range from 3.6 to 3.8% by weight.

With regard to the form in which the catalyst according to the present invention is present, there are likewise no restrictions whatsoever, and so the one or more zeolites and the particles of the one or more metal oxides present therein may in principle be combined in any possible and suitable manner to give a catalyst, the form preferably being selected such that the catalyst is suitable at least in one of the particular or preferred uses as described in the present application and especially for the use of a catalyst for converting oxygenates to olefins. In this context, the catalyst is preferably in the form of a shaped body comprising a mixture of the one or more zeolites of the MFI, MEL and/or MWW structure type and the particles of the one or more metal oxides, preferably of the one or more zeolites and the particles of the one or more metal oxides according to one of the particular or preferred embodiments as described in the present application. In a particularly preferred embodiment of the present invention, the shaped body is an extrudate.

Thus, according to the present invention, it preferred that the catalyst for the conversion of oxygenates to olefins, and especially the catalyst according to one of the particular and preferred embodiments of the present invention, is in the form of a shaped body comprising a mixture of the one or more zeolites of the MFI, MEL and/or MWW structure type and of the particles of the one or more metal oxides.

According to the present invention, the catalyst displays a water uptake of 9.0 wt.-% or less. Thus, the catalyst for the conversion of oxygenates to olefins according to the present invention displays a low water uptake, i.e. a high hydrophobicity, wherein it is preferred that the catalyst displays a water uptake of 8.0 wt.-% or less, more preferably of 7.0 wt.-% or less, more preferably of 6.0 wt.-% or less, and more preferably of 5.5 wt.-% or less, wherein more preferably the catalyst displays a water uptake ranging from 0.5 to 5.0 wt.-%, more preferably of from 1.0 to 4.5 wt.-%, more preferably of from 1.5 to 4.0 wt.-%, and more preferably of from 2.0 to 3.5 wt.-%. According to the present invention it is however particularly preferred that the catalyst for the conversion of oxygenates to olefins displays a water uptake ranging from 2.5 to 3.0 wt.-%.

Within the meaning of the present invention, the water uptake of a material and in particular of a zeolitic material as defined in any of the particular and preferred embodiments of the present invention expressed in wt.-% preferably refers to the water uptake of a material at 85 wt.-% relative humidity (RH) expressed in increase in weight compared to the dry sample, i.e. the weight of the sample measured at 0% RH. According to the present invention it is preferred that the weight of the sample measured at 0% RH refers to the sample from which residual moisture has been removed by heating the sample to 100° C. (heating ramp of 5° C./min) and holding it for 6 h under a nitrogen flow. According to the present invention it is particularly preferred that the water uptake of a material as defined for any of the particular and preferred embodiments of the inventive process refers to the water uptake of a material and in particular of a zeolitic material at 85% RH as obtained according to the procedure for the measurement of the water adsorption/desorption isotherms as described in the experimental section of the present application.

The catalyst according to the present invention can be prepared in any suitable manner, provided that it comprises one or more zeolites of the MFI, MEL and/or MWW structure type and particles of one or more metal oxides according to the present invention and especially according to any one of the particular or preferred embodiments of the invention as described in the present application. Preference is given to preparing the catalyst in the form of a shaped body comprising a mixture of the one or more zeolites of the MFI, MEL and/or MWW structure type and the particles of the one or more metal oxides according to the present invention and especially according to any one of the particular or preferred embodiments as described in the present application with respect to the one or more zeolites and/or the particles of the one or more metal oxides.

Thus, the present invention also relates to a process for preparing a catalyst according to the present invention, and especially a catalyst according to any one of the particularly preferred embodiments thereof, comprising (I) providing a catalyst comprising one or more zeolites of the MFI, MEL and/or MWW structure type and particles of one or more metal oxides, the one or more zeolites of the MFI, MEL and/or MWW structure type comprising one or more alkaline earth metals selected from the group consisting of Mg, Ca, Sr, Ba and combinations of two or more thereof; and (II) treating the catalyst with one or more silylating agents;

(III) optionally calcining the silylated catalyst obtained in (II).

As regards step (I) of the inventive process for preparing a catalyst according to the present invention, no particular restrictions apply relative to the one or more zeolites of the MFI, MEL and/or MWW structure type, nor with respect to the one or more alkaline earth metals selected from the group consisting of Mg, Ca, Sr, Ba and combinations of two or more thereof, nor with respect to the particles of one or more metal oxides which may be respectively employed therein, provided that a catalyst may be obtained displaying a water uptake of 9.0 wt.-% or less in the inventive process. According to the present invention, it is however preferred that the catalyst provided in step (I) is a catalyst according to any of the particularly preferred embodiments of the present invention as described in the foregoing sections, in particular relative to the one or more zeolites of the MFI, MEL and/or MWW structure type as well as with respect to the one or more metal oxides and to the one or more alkaline earth metals selected from the group of Mg, Ca, Sr, Ba, and combinations of two or more thereof.

It is, however, particularly preferred according to the inventive process for the preparation of a catalyst for the conversion of oxygenates to olefins that the catalyst provided in step (I) is obtainable and/or obtained according to a process comprising (I.a) providing one or more zeolites of the MFI, MEL and/or MWW structure type;
(I.b) impregnating the one or more zeolites of the MFI, MEL and/or MWW structure type with a solution comprising the one or more alkaline earth metals, preferably by means of spray impregnation;
(I.c) optionally drying the one or more impregnated zeolites obtained in (I.b);
(I.d) optionally calcining the one or more impregnated zeolites obtained in (I.b) or (I.c);
(I.e) preparing a mixture comprising the one or more impregnated and optionally dried and/or calcined zeolites of the MFI, MEL and/or MWW structure type, one or more solvents and particles of the one or more metal oxides and/or precursor compounds of the one or more particles of the one or more metal oxides;
(I.f) homogenizing the mixture obtained in (I.e);
(I.g) extruding the homogenized mixture obtained in (I.f);
(I.h) optionally drying the extrudate obtained in (I.g);
(I.i) optionally calcining the extrudate obtained in (I.g) or (I.h).

According to the present invention it is particularly preferred that the catalyst provided in step (I) of the inventive process for preparing a catalyst is obtained according to a process comprising steps (I.a)-(I.i), and in particular that step (I) of the inventive process comprises steps (I.a)-(I.i).

With regard to the form in which the one or more zeolites of the MFI, MEL and/or MWW structure type are provided in step (I.a), there is no restriction whatsoever in principle, especially with respect to the further elements or compounds which may be present therein. Thus, there are generally no restrictions whatsoever with regard to the ions and compounds which may be present in the micropores of the one or more zeolites, especially with respect to the counterions to the possibly negatively charged zeolite framework which are present in the micropores. Accordingly, the one or more zeolites may be in a form in which the possibly negative charge of the zeolite framework is compensated for by one or more different cationic elements and/or compounds, this preferably being accomplished at least partly by means of one or more cationic elements and/or compounds selected from the group consisting of $H^+$, $NH_4^+$, $Li^+$, $Na^+$, $K^+$ and combinations of two or more thereof, further preferably from the group consisting of $H^+$, $Na^+$, $K^+$ and combinations of two or more thereof. In particularly preferred embodiments of the present invention, the one or more zeolites of the MFI, MEL and/or MWW structure type optionally comprise $H^+$ and/or $Na^+$, and preferably $H^+$ as the counterion to the negatively charged zeolite framework, which means that the one or more zeolites of the MFI, MEL and/or MWW structure type are more preferably provided in the respective H form thereof in step (I.a) of the process according to the invention.

In the particularly preferred embodiments of the present invention according to which the one or more zeolites of the MFI, MEL and/or MWW structure type in step (I.a) are each provided at least partly in the H form thereof, these can be converted to the desired H form by corresponding ion exchange. In the preferred embodiments of the process for preparing the catalyst according to which the one or more zeolites for the provision in (I.a) are optionally converted to the H form, there are no particular restrictions in principle with respect to the manner in which this is conducted, the conversion of the one or more zeolites preferably being effected by ion exchange. With respect to the preferred embodiments of the process for preparing the catalyst according to which the conversion of the one or more zeolites of the MFI, MEL and/or MWW structure type to the H form is effected over one or more ion exchange steps for the provision in step (I.a), there are again no particular restrictions with respect to the manner in which this is conducted, provided that at least some of the counterions to the zeolite framework can be exchanged for H+ ions. In preferred embodiments, for the purpose of ion exchange, the one or more zeolites are contacted with a solution of a protonated volatile base, preferably of a protonated volatile amine, more preferably with an ammonium salt solution, or alternatively with an acid and preferably with an aqueous acid solution, preferably with an aqueous solution of a mineral acid. With respect to the ammonium salts which are preferably used, there is no general restriction, provided that the exchange of at least some of the counterions present in the one or more zeolites for ammonium can be accomplished. For example, it is possible for this purpose to use one or more ammonium salts selected from the group consisting of $NH_4NO_3$, $NH_4Cl$, $(NH_4)_2SO_4$ and mixtures of two or more thereof. The same applies correspondingly with respect to the acids and especially the mineral acids which can be used for the purpose of ion exchange, provided that the exchange of at least some of the counterions present in the one or more zeolites for $H^+$ can be accomplished. Thus, it is possible to use, for example, solutions of the mineral acids $HNO_3$, $HCl$, $H_2SO_4$, and also mixtures of two or more thereof for the ion exchange. With respect to the concentration of the solutions of protonated volatile bases or of acids used for the preferred ion exchange, there is no particular restriction whatsoever, provided that at least some of the counterions of the zeolite framework can be exchanged, and, in the case of use of one or more acids, that the pH of the solution does not lead to any significant dissolution of the zeolite framework. Thus, it is possible to use, for example, solutions of the salts or of the acids having a concentration of 1 to 50% by weight, preference being given to using concentrations of 5 to 30% by weight and more preferably of 10 to 25% by weight for the ion exchange. The same applies correspondingly with respect to the weight ratio of salt solution or acid solution to the one or more zeolites which are ion-exchanged. Thus, the weight ratio of the solution used for the ion exchange to the one or more zeolites may, for example, be in the range from 1 to 20, the weight ratio preferably being in the range from 2 to 10 and further preferably in the range from 4 to 7.

In particularly preferred embodiments, an ion exchange is thus performed prior to provision of the one or more zeolites in step (I.a). In the particularly preferred embodiments of the preparation of the catalyst used in the process according to the invention in which an ion exchange step with a protonated volatile base, and preferably with a protonated volatile amine, more preferably with ammonium, is performed, it is further preferred that, after the ion exchange and an optional wash step and/or after an optional drying step, a further calcining step is performed in order to remove the volatile base and more preferably ammonia completely from the ion-exchanged zeolite.

With regard to the manner of impregnation in step (I.b) and in (I.i) of the process according to the invention, the impregnation can be performed by any suitable process, for example an impregnation by soaking, spray impregnation and/or capillary impregnation. In particularly preferred embodiments of the process according to the invention, however, the impregnation in step (I.b) is achieved by spray impregnation.

With regard to the solids concentration of the mixture provided in (I.e) or (I.e.3), according to the present invention, there are no particular restrictions whatsoever, provided that homogenizing of the mixture according to step (I.f) and extrusion in (I.g) of the homogenized mixture obtained in (I.f) are possible. Thus, the solids concentration of the mixture provided in (I.e) or (I.e.3) may, for example, be in the range of 40-85% by weight, the solids concentration according to the present invention preferably being in the range of 50-75% by weight and further preferably in the range of 55-70% by weight. In particularly preferred embodiments of the process according to the invention for preparing a catalyst, the solids concentration of the mixture provided in (I.e) or (I.e.3) is in the range of 60-65% by weight.

With regard to the homogenizing in step (I.f), according to the present invention, there is no particular restriction whatsoever, and so it is possible to select any conceivable procedure in order to obtain a homogeneous mixture of the mixture prepared in step (I.e) or (I.e.3), for which purpose it is possible to use, for example, one or more processes selected from the group consisting of stirring, kneading, agitating, vibration or a combination of two or more thereof. According to the present invention, the mixture prepared in step (I.e) or (I.e.3) is preferably homogenized by stirring and/or by kneading in step (I.f), particular preference being given to homogenizing in step (I.f) by kneading.

In preferred embodiments of the process according to the invention for preparing a catalyst, in the preparation of the mixture in step (I.e), a first mixture comprising the one or more impregnated and optionally dried and/or calcined zeolites of the MFI, MEL and/or MWW structure type and the particles of the one or more metal oxides and/or precursor compounds of the one or more particles of the one or more metal oxides is first prepared, this preferably being treated with a peptizing aid prior to addition of the one or more solvents, the peptizing preferably being performed by means of an acid treatment. With regard to the acid used for the preferred acid treatment, according to the present invention, there is no particular restriction whatsoever with respect to the amount or type of the acid which is used for the acid treatment, this being selected in each case such that the components of the first mixture are merely etched and the one or more zeolites and the particles of the one or more metal oxides and/or precursor compounds are attacked only insignificantly thereby, more particularly such that the action thereof as a catalyst is not substantially restricted thereby. According to the present invention, preference is thus given to using weak acids and especially short-chain carboxylic acids for this purpose, preferably (C1-C4)-carboxylic acids, further preferably (C1-C3)-carboxylic acids, further preferably acetic and/or formic acid, and especially formic acid is used for the preferred acid treatment.

According to the present invention it is however further preferred that in step (I.e) a mixture comprising the one or more impregnated and optionally dried and/or calcined zeolites of the MFI, MEL and/or MWW structure type and particles of the one or more metal oxides and/or precursor compounds of the one or more particles of the one or more metal oxides is first provided in a step (I.e.1) and subsequently admixed in a step (I.e.2) with one or more acids of phosphorus prior to mixing the mixture obtained in (I.e.2) with one or more solvents in a step (I.e.3). In particular, it is preferred that the peptizing is effected by means of this step, in addition to introducing phosphorous into the mixture for obtaining a phosphorous containing catalyst. With regard to the acid or acids of phosphorus used for the acid treatment, there is no particular restriction according to the present invention with regard to the amount or type of the acid or acids of phosphorus which are used for the acid treatment, these preferably being selected such that the components of the first mixture are merely etched and the one or more zeolites and the particles of the one or more metal oxides and/or precursor compounds thereof are attacked only insignificantly thereby, more particularly such that the action thereof as a catalyst is not substantially restricted as a result. According to the present invention, it is thus possible in principle to use any suitable acid of phosphorus, and also any suitable mixture of two or more acids of phosphorus. In particular embodiments of the alternative of the process according to the invention, one or more acids of phosphorus selected from the group consisting of phosphinic acid, phosphonic acid, phosphoric acid, peroxophosphoric acid, hypodiphosphonic acid, diphosphonic acid, hypodiphosphoric acid, diphosphoric acid, peroxodiphosphoric acid and mixtures of two or more thereof are used in (I.e.2). Further preferably, one or more acids of phosphorus selected from the group consisting of phosphonic acid, phosphoric acid, diphosphonic acid, disphosphoric acid and mixtures of two or more thereof are used, further preferably from the group consisting of phosphoric acid, diphosphoric acid and mixtures thereof, and, in particularly preferred embodiments of the alternative of the process according to the invention in which the mixture obtained in (I.e.1) is admixed in (I.e.2) with one or more acids of phosphorus, phosphoric acid is used for this purpose.

Therefore, it is further preferred according to the present invention that step (I.e) comprises
(I.e.1) preparing a mixture comprising the one or more impregnated and optionally dried and/or calcined zeolites of the MFI, MEL and/or MWW structure type and particles of the one or more metal oxides and/or precursor compounds of the one or more particles of the one or more metal oxides;
(I.e.2) admixing the mixture obtained in (I.e.1) with a phosphorus-comprising solution, preferably with phosphoric acid;
(I.e.3) mixing the mixture obtained in (I.e.2) with one or more solvents.

In further preferred embodiments of the process according to the invention for preparing a catalyst, a plasticizing aid is used for the preparation of the mixture in (I.e) or (I.e.3). With regard to the viscosity additives and especially the plasticizing aids which can be used in the preferred embodiments of the process according to the invention, there are no particular restrictions, provided that they are suitable for influencing the viscosity of the mixture in the desired manner, and especially in order to establish a viscosity of the mixture obtained in (I.e) or (I.e.3) and especially of the homogenized mixture obtained in (I.f) suitable for the extrusion of the homogenized mixture in step (I.g). Particular preference is given to using viscosity additives and especially the plasticizing aids according to the present invention which can be removed from the extrudate at least partly and preferably substantially without residue, especially by the optional drying step in (I.h) and/or by the optional calcining step in step (I.i), and preference is further given to using a plasticizing aid which volatilizes out of the extrudate in step (I.h) and/or (I.i) and/or decomposes as a result of thermolysis in step (I.h) in the case of preferred heating of the extrudate and/or in step (I.i) as a result of pyrolysis to give volatile compounds and especially to gases which can correspondingly escape from the extrudate. Thus, according to the preferred embodiments, it is possible in principle to use any suitable substance or any suitable substance mixtures as plasticizing aids, preference being given to using those which, according to the particular and preferred embodiments of the process according to the invention for preparing a catalyst, can be removed from the extrudate at least partly and preferably substantially without residue. The plasticizing aids used are thus preferably organic substances or substance mixtures and especially organic polymers, and further preferably starch derivatives.

As regards the one or more plasticizing aids which are preferably used for the preparation of the mixture in (I.e) or (I.e.3), in principle no particular restriction applies neither with respect to the type, nor with respect to the amount thereof which may be employed, such that any suitable plasticizing aid may be employed in any suitable amount. Thus, by way of example, the one or more plasticizing aids may be selected from the group consisting of polymers, carbohydrates, graphite, and mixtures of two or more thereof, wherein preferably the one or more plasticizing agents are selected from the group consisting of polymeric vinyl compounds, polyalkylene oxides, polyacrylates, polyolefins, polyamides, polyesters, cellulose and cellulose derivatives, sugars, and mixtures of two or more thereof, more preferably from the group consisting of polystyrene, C2-C3 polyalkylene oxides, cellulose derivatives, sugars, and mixtures of two or more thereof, more preferably from the group consisting of polystyrene, polyethylene oxide, C1-C2 hydroxyalkylated and/or C1-C2 alkylated cellulose derivatives, sugars, and mixtures of two or more thereof, more preferably from the group consisting of polystyrene, polyethylene oxide, hydroxyethyl methyl cellulose, and mixtures of two or more thereof. According to the inventive process, it is particularly preferred that the one or more plasticizing agents preferably added in (I.e) or (I.e.3) is selected from the group consisting of polystyrene, polyethylene oxide, hydroxyethyl methyl cellulose, and mixtures of two or more thereof, wherein it is yet further preferred that the one or more plasticizing agents consist of one or more selected from the group consisting of polystyrene, polyethylene oxide, hydroxyethyl methyl cellulose, and mixtures of two or more thereof, wherein more preferably the one or more plasticizing agents consist of hydroxyethyl methyl cellulose.

According to the present invention it is further preferred that phosphorous is added to the catalyst after extrusion thereof in step (I.g), and optional drying and/or calcination thereof in steps (I.h) and (I.i), respectively. Therefore, it is further preferred according to the inventive process that step (I) further comprises (I.j) impregnating the optionally dried and/or calcined extrudate with a phosphorus-comprising solution, preferably with phosphoric acid;

(I.k) optionally drying the impregnated extrudate obtained in (I.j);

(I.l) optionally calcining the extrudate obtained in (I.j) or (I.k).

With regard to the preferred impregnation of the optionally dried and/or calcined extrudate in step (I.j) or the admixing of the mixture obtained in (I.e.1) in step (I.e.2) with a phosphorus-comprising solution, there is no particular restriction whatsoever with respect to the phosphorus-comprising solution which can be used for this purpose, wherein preferably the impregnation leads, after optional drying in step (I.k) or (I.h) and/or optional calcining in step (I.l) or (I.i), to an at least partly oxidic form of the phosphorus present in the particles of the one or more metal oxides. Thus, it is possible in principle to use any suitable phosphorus-comprising solution for this purpose. According to the present invention, it is possible to use, for example, phosphorus- and oxygen-containing salts and/or acids, the solubility being based especially on the particular and preferred solvents according to the present invention which are used especially in step (I.j) or (I.e.2) of the process according to the invention. Thus, it is possible to use solutions of phosphinates, phosphonates, phosphates, peroxophosphates, hypodiphosphonates, diphosphonates, hypodiphosphates, diphosphates, peroxodiphosphates and mixtures of two or more thereof, in each case as salts and/or acids.

According to the present invention, however, it is preferable to use a solution and especially an aqueous solution of a phosphorus- and oxygen-comprising salt and/or acid which is/are derived from the salts selected from the group of the phosphonates, phosphates, diphosphonates, diphosphates and mixtures of two or more thereof, and especially a phosphorus-comprising solution is used in step (I.j) or (I.e.2) which comprises one or more acids of phosphorus, preferably selected from the group consisting of phosphonic acid, phosphoric acid, diphosphonic acid, diphosphoric acid and mixtures of two or more thereof, preferably as an aqueous solution. Particular preference is given to using phosphoric acid solutions for impregnation of the optionally dried and/or calcined extrudate in step (I.j) or for the admixing of the mixture obtained in (I.e.1) in step (I.e.2) of the process according to the invention, preferably aqueous phosphoric acid solutions.

With regard to the phosphorus-comprising solutions preferably used in the preferred embodiments of the inventive process, there is no restriction whatsoever in principle with respect to the concentration of phosphorus present therein, provided that suitable impregnation of the optionally dried and/or calcined extrudate can be achieved in step (I.j) or that it is suitable for admixing the mixture obtained in (I.e.1) in step (I.e.2). In the preferred embodiments of the present invention in which phosphorus- and oxygen-containing salts and/or acids are used, it is thus possible, for example, to use total concentrations of the phosphorus- and oxygen-containing salts and/or acids in the solutions in the range from 0.1 to 90% by weight of the solution used and preferably of the aqueous solutions used. According to the present invention, however, preference is given to using concentrations of the phosphorus- and oxygen-containing salts and/or acids according to the particular and preferred embodiments of the invention in the range from 0.5 to 70% by weight, further preferably from 1 to 50% by weight, further preferably from 5 to 40% by weight, further preferably from 10 to 35% by weight, further preferably from 15 to 30% by weight and even further preferably from 18 to 25% by weight. In particularly preferred embodiments of the process according to the invention, the concentration of the preferred phosphorus- and oxygen-containing salts and/or acids in step (I.j) of the process according to the invention is in the range from 19 to 22% by weight based on the total weight of the solution used. In the alternative of the process according to the invention in which the mixture obtained in (I.e.1) is admixed in (I.e.2) with a phosphorus-comprising solution, preferably with one or more acids of phosphorus and further preferably with phosphoric acid, preference is given to using total concentrations of the phosphorus- and oxygen-containing salts and/or acids in the solutions in the range from 5 to 99% by weight of the solution used and preferably of the aqueous solutions used. According to the present invention, however, preference is given to using concentrations of the phosphorus- and oxygen-containing salts and/or acids as per the particular and preferred embodiments of the invention in the range from 10 to 98% by weight, further preferably from 30 to 95% by weight, further preferably from 50 to 92% by weight, further preferably from 60 to 90% by weight, further preferably from 70 to 89% by weight and even further preferably from 80 to 88% by weight. In particularly preferred embodiments of the process according to the invention, the concentration of the preferred phosphorus- and oxygen-containing salts and/or acids in step (I.j) of the process according to the invention is in the range from 83 to 87% by weight based on the total weight of the solution used.

In particular embodiments of the inventive process in which the mixture obtained in (I.e.1) is admixed in (I.e.2) with a phosphorus-comprising solution, the optionally dried and/or calcined extrudate which is obtained correspondingly in (I.g), (I.h) and/or (I.i) is then impregnated in a subsequent step (I.j) with a phosphorus-comprising solution in the process according to the invention or the particular and preferred embodiments thereof. In accordance with the process according to the invention, in these preferred embodiments, the impregnated extrudate obtained in (I.j) is optionally dried in a further step (I.k) in the process according to the invention or the particular and preferred embodiments thereof, and optionally calcined in a further step (I.l) in the process according to the invention or the particular and preferred embodiments thereof. Accordingly, the preparation in the embodiments mentioned includes a double introduction of the phosphorus into the one or more metal oxides and/or precursor compounds thereof in (I.e.2) and in (I.j). However, particular preference is given to embodiments of the process according to the invention for preparing the inventive catalyst in which no impregnation of the extrudate obtained in (I.g), (I.h) and/or (I.i) with phosphorus or a phosphorus-containing compound is effected, such that a particularly efficient process for preparing the inventive catalyst is provided.

In the process according to the invention for preparing the inventive catalyst, especially in the particular and preferred embodiments described in the present application, there is in principle no restriction whatsoever with regard to the properties and especially the particle sizes and/or morphologies of the one or more zeolites of the MFI, MEL and/or MWW structure type provided in step (I.a). According to the particle size of the zeolites provided in step (I.a), however, one or more steps are optionally performed during the process according to the invention, preferably after the impregnation in step (I.b) or after the optional drying in step (I.c) or after the optional calcining in step (I.d), in order to bring the one or more zeolites to a preferred particle size. In this connection, there is at first no particular restriction with regard to the particle size of the one or more zeolites, provided that this is suitable for the performance of the further steps in the process according to the invention, especially according to the particular and preferred embodiments of the present invention, and the particle size should especially be suitable for performance of the extrusion in step (I.g), more particularly depending on the size and/or shape of the extruded body. Thus, in particular embodiments of the process according to the invention, one or more steps are performed after the impregnation in step (I.b) or after the optional drying in step (I.c) or after the optional calcining in step (I.d), in order to bring the one or more impregnated and optionally dried and/or calcined zeolites of the MFI, MEL and/or MWW structure type to a particle size D50 in the range from 5 to 1000 µm. In further preferred embodiments of the process according to the invention, the one or more zeolites are brought after one or more of the aforementioned steps, in one or more steps, to a particle size $D_{50}$ in the range from 10 to 750 µm, further preferably from 30 to 500 µm, further preferably from 50 to 300 µm, further preferably from 70 to 200 µm and even further preferably from 80 to 150 µm. In yet further preferred embodiments of the process according to the invention, the one or more impregnated and optionally dried and/or calcined zeolites, after the impregnation in step (I.b) or after the drying in step (I.c) or after the calcining in step (I.d), is brought in one or more steps to a particle size D50 in the range from 90 to 120 µm. With regard to the number of steps and the manner in which the one or more zeolites are brought to a particular or preferred particle size $D_{50}$, according to the present invention, there are no restrictions whatsoever, and so it is possible in principle to use any suitable process for this purpose. According to the present invention, however, the one or more zeolites are preferably subjected to one or more milling steps after one or more of steps (I.b) and optional steps (I.c) and (I.d).

Thus, according to the present invention, preference is given to embodiments of the process for preparing a catalyst according to the present invention, and especially a catalyst according to one of the particular or preferred embodiments thereof, in which the impregnating in (I.b) or the drying in (I.c) or the calcining in (I.d) is followed by bringing of the one or more impregnated zeolites of the MFI, MEL and/or MWW structure type to a particle size $D_{50}$ in the range from 5 to 1000 µm, further preferably from 10 to 750 µm, further preferably from 30 to 500 µm, further preferably from 50 to 300 µm, further preferably from 70 to 200 µm, further preferably from 80 to 150 µm, even further preferably from 90 to 120 µm, preferably by milling.

According to the present invention, in the process according to the invention, a drying step is performed according to one or more of steps (I.c), (I.h) and/or (I.k). With regard to the manner in which the optional drying is achieved in one or more of these steps, there is no restriction whatsoever in principle, and so the drying can be performed at any suitable temperature and in any suitable atmosphere. Thus, the optional drying can be effected under a protective gas atmosphere or in air, the optional drying preferably being effected in air. With regard to the temperature at which the drying is effected, it is possible, for example, to select a temperature in the range from 50 to 220° C. According to the present invention, the optional drying according to one or more of steps (I.c), (I.h) and/or (I.k) is effected at a temperature in the range from 70 to 180° C., further preferably from 80 to 150° C., further preferably from 90 to 130° C. and further preferably in the range from 100 to 125° C. In particularly preferred embodiments of the process according to the invention, the drying according to one or more of steps (I.c), (I.h) and/or (I.k) is effected at a temperature in the range from 110 to 120° C. With regard to the duration of the one or more optional drying steps, especially in particular and preferred embodiments of the process according to the invention, there is no particular restriction, provided that drying suitable for the further process steps can be achieved, for example after a drying step having a duration of 1 to 50 hours. In particular embodiments of the process according to the invention, the optional drying is performed for a period of 5 to 40 h, further preferably of 8 to 30 h, further preferably of 10 to 25 h, further preferably of 12 to 20 h and still further preferably of 14 to 18 h.

Thus, according to the present invention, preference is given to embodiments of the process for preparing a catalyst according to the present invention, and especially a catalyst according to one of the particular or preferred embodiments thereof, in which the drying in (I.c), (I.h) and/or (I.k) is effected at a temperature in the range from 50 to 220° C., preferably from 70 to 180° C., further preferably from 80 to 150° C., further preferably from 90 to 130° C., further preferably from 100 to 125° C., and further preferably from 110 to 120° C.

With regard to the optional calcining steps according to the present invention, the same applies in principle as with regard to the optional drying steps, and so no particular restriction whatsoever exists here either, either with regard to the temperature or with regard to the atmosphere in which the calcination is performed, and finally also not with regard to the duration of a calcination according to the particular and preferred embodiments of the present invention, provided that the product of the calcination is an intermediate suitable for being processed in the further steps of the process according to the invention to give a catalyst according to the present invention. Thus, for example, with regard to the temperature of the optional calcining in one or more of the optional steps (I.d), (I.i) and/or (I.l), a temperature in the range from 300 to 850° C. may be selected, preference being given to selecting a temperature in the range from 350 to 750° C., further preferably from 400 to 700° C., further preferably from 450 to 650° C. and even further preferably from 480 to 600° C. In yet further preferred embodiments of the present invention, the calcination in one or more of the optional steps (I.d), (I.i) and/or (I.l) is performed at a temperature of 500 to 550° C. With regard to the atmosphere in which the optional calcination according to one or more of the aforementioned steps of the process according to the invention is performed, this may be either an inert atmosphere or air, the optional calcination in one or more of the optional steps (I.d), (I.i) and/or (I.l) preferably being performed in air. Finally, there is also no restriction whatsoever with regard to the duration of the calcination step in the optional steps (I.d), (I.i) and/or (I.l), provided that the product of the calcination is suitable for further use, especially as an intermediate according to the optional steps (I.d) and/or (I.i), in the process according to the invention for preparing a catalyst, especially a catalyst according to one of the particular or preferred embodiments of the present application. Thus, the duration of the calcination according to one or more of the optional calcination steps in (I.d), (I.i) and/or (I.l) may, for example, be 0.5 to 20 hours, preference being given to a duration of 1 to 15 h, further preferably of 2 to 10 h, further preferably of 3 to 7 h, and particular preference to a duration of 4 to 5 h.

Thus, according to the present invention, preference is given to embodiments of the process for preparing a catalyst according to the present invention, and especially a catalyst according to one of the particular or preferred embodiments thereof, in which the calcining in (I.d), (I.i) and/or (I.l) is effected at a temperature in the range from 300 to 850° C., preferably from 350 to 750° C., further preferably from 400 to 700° C., further preferably from 450 to 650° C., further preferably from 480 to 600° C., and further preferably from 500 to 550° C.

In steps (I.b) and (I.j) of the process according to the invention, the one or more zeolites of the MFI, MEL and/or MWW structure type are first impregnated with a solution comprising one or more alkaline earth metals, or the optionally dried and/or calcined extrudate is impregnated with a phosphorus-comprising solution. According to the present invention, there is no restriction whatsoever either with respect to step (I.b) or with respect to step (I.j) with regard to the type and/or number of solvents used for this purpose. Thus, it is possible in principle to use any suitable solvent or solvent mixture in steps (I.b) and (I.j), provided that it is suitable for bringing about a corresponding impregnation of the materials defined therein, especially according to the particular and preferred embodiments of the present invention. This is equally true of the one or more solvents which are used in step (I.e) or (I.e.3) for preparation of the mixture defined therein, provided that the one or more solvents used for this purpose are suitable for enabling homogenization in step (I.f) and the extrusion in step (I.g). For example, it is possible in one or more of steps (I.b), (I.j) and/or (I.e) or (I.e.3) to use one or more solvents selected from the group consisting of alcohols, water, mixtures of two or more alcohols and mixtures of water and one or more alcohols. In preferred embodiments of the present invention, the one or more solvents used in (I.b), (I.j) and/or (I.e) or (I.e.3) are selected from the group consisting of $(C_1-C_6)$-alcohols, water, mixtures of two or more $(C_1-C_6)$-alcohols and mixtures of water and one or more $(C_1-C_6)$-alcohols, the one or more solvents further preferably being from the group consisting of $(C_1-C_4)$-alcohols, water, mixtures of two or more $(C_1-C_4)$-alcohols and mixtures of water and one or more $(C_1-C_4)$-alcohols. In further preferred embodiments, the one or more solvents in steps (I.b), (I.j) and/or (I.e) or (I.e.3) are selected from the group consisting of methanol, ethanol, n-propanol, isopropanol, water and mixtures of two or more thereof, further preferably from the group consisting of methanol, ethanol, water and mixtures of two or more thereof, the solvent even further preferably being water, preferably distilled water.

Thus, according to the present invention, preference is given to embodiments of the process for preparing a catalyst according to the present invention, and especially a catalyst according to one of the particular or preferred embodiments thereof, in which the solution used in (I.b) and/or (I.j) or (I.e2) and/or the mixture prepared in (I.e) or (I.e.3) comprises one or more solvents selected from the group consisting of alcohols, water, mixtures of two or more alcohols, and mixtures of water and one or more alcohols, preferably from the group consisting of $(C_1-C_8)$ alcohols, water, mixtures of two or more $(C_1-C_6)$ alcohols, and mixtures of water and one or more $(C_1-C_6)$ alcohols, further preferably $(C_1-C_4)$ alcohols, water, mixtures of two or more $(C_1-C_4)$ alcohols, and mixtures of water and one or more $(C_1-C_4)$ alcohols, further preferably consisting of methanol, ethanol, n-propanol, isopropanol, water and mixtures of two or more thereof, further preferably consisting of methanol, ethanol, water and mixtures of two or more thereof, the solvent further preferably being water, preferably distilled water.

In step (II) of the inventive process for preparing a catalyst, the catalyst provided in step (I) is treated with one or more silylating agents. According to the present invention, no particular restriction applies relative to the one or more silylating agents which may be employed for the treatment of the catalyst in step (II), such that in principle any suitable silylating agent or combination of silylating agents may be employed, provided that the catalyst provided in step (I) is at least in part silylated during the course of the treatment in step (II). Thus, by way of example, the one or more silylating agents are preferably selected from the group consisting of alkyldisilazanes, alkylalkoxysilanes, haloalkylsilanes, and mixtures of two or more thereof. According to the inventive process for the preparation of a catalyst it is however particularly preferred that the one or more silylating agents comprise one or more alkyldisilazanes, wherein even more preferably the one or more silylating agents consist of one or more alkyldisilazanes.

Concerning the alkylalkoxysilanes preferably comprised among the one or more silylating agents, no particular restriction applies, neither with respect to the type nor with respect to the number of specific alkylalkoxysilanes which may be employed as silylating agents in step (II) of the inventive process. In particular, there is no particular restriction as to the number of alkyl and alkoxy chains which may be present among the four silane rests, wherein it is preferred that the one or more alkylalkoxysilanes are selected from the group consisting of trialkylalkoxysilanes, alkyltrialkoxysilanes, and mixtures of two or more thereof. Furthermore, as regards the alkyl and alkoxy rests which are respectively present in the alkylalkoxysilanes, again no particular restriction applies relative to the length of the alkyl and alkoxy chains, provided that the one or more alkylalkoxysilanes are capable of reacting with the catalyst in step (II) of the inventive process such that at least a portion thereof may be silylated. Furthermore, no restriction applies as to whether said alkyl and alkoxy rests are branched or unbranched, or as to whether they are substituted by other moieties than hydrogen. Thus, by way of example, the alkyl chains may be selected from the group consisting of optionally branched and/or optionally substituted $(C_1-C_6)$alkyl, wherein preferably the alkyl chains are independently from one another selected from the group consisting of optionally branched and/or optionally substituted $(C_1-C_5)$alkyl, more preferably $(C_1-C_4)$alkyl, and more preferably optionally branched and/or optionally substituted $(C_1-C_3)$alkyl. According to the present invention it is however preferred that the alkyl chains are independently from one another selected among unsubstituted alkyl and more preferably un-substituted and unbranched alkyl, wherein more preferably the alkyl groups are independently from one another selected from the group consisting of methyl, ethyl, or propyl, wherein more preferably the alkyl groups are selected from ethyl and methyl. Thus, according to the inventive process for the production of a catalyst it is particularly preferred that the alkylalkoxysilanes are selected from the group consisting of methoxytrimethylsilane, ethoxytrimethylsilane, propoxytrimethylsilane, methyltrimethoxysilane, methyltriethoxysilane, ethyltrimethoxysilane, ethyltriethoxysilane, propyltrimethoxysilane, propyltriethoxysilane, and mixtures of two or more thereof, wherein according to the present invention it is particularly preferred that the alkylalkoxysilanes are selected from the group consisting of methoxytrimethylsilane, ethoxytrimethylsilane, methyltrimethoxysilane, methyltriethoxysilane, ethyltrimethoxysilane, ethyltriethoxysilane, and mixtures of two or more thereof.

Regarding the haloalkylsilanes preferably comprised among the one or more silylating agents employed in step (II) of the inventive process, as for the alkylalkoxysilanes, no particular restriction applies neither with respect to their number nor with respect to the specific type of haloalkylsilanes which may be employed, provided that at least a portion of the catalyst treated in step (II) is silylated when contacted with said one or more haloalkylsilanes. Thus, there is no particular restriction relative to the type or number of halo groups nor with respect to the type or number of alkoxy groups contained therein, such that independently from one another the four residues of said silane compounds may be a halo group or an alkyl group. According to the present invention it is however preferred that the haloalkylsilanes are selected from the group consisting of dihalodialkylsilanes. As regards the alkyl chains present in the haloalkylsilanes or preferably in the dihalodialkylsilanes, no particular restriction applies such that in principle there is no restriction relative to the number of carbon atoms in the alkyl chain nor as to whether said chain is branched or unbranched, or as to whether independently thereof the alkyl chain is substituted or not. Thus, by way of example, the alkyl chains may be selected from the group consisting of optionally branched and/or optionally substituted (C1-C6)alkyl, wherein preferably the one or more alkyl chains are independently from one another selected from the group consisting of optionally branched and/or optionally substituted (C1-C5)alkyl, more preferably (C1-C4)alkyl, and more preferably optionally branched and/or optionally substituted (C1-C3)alkyl. According to the present invention it is further preferred that the alkyl groups of the haloalkylsilanes are non-substituted alkyl groups, and more preferably unbranched and unsubstituted alkyl groups, such that it is particularly preferred that the alkyl groups are independently from one another selected from the group consisting of methyl, ethyl, or propyl, and even more preferably wherein the alkyl groups are independently from one another selected from ethyl and methyl. As regards the one or more halo groups contained in the alkylsilanes, these are independently from one another selected from the group consisting of halogens and pseudohalogens, preferably from the group consisting of CN, F, Cl, Br, and I, and more preferably from the group consisting of CN, Cl, and Br, wherein even more preferably the halo groups are, independently from one another Cl or Br, the one or more halo groups particularly preferably being Cl. Thus, according to the inventive process wherein the one or more silylating agents comprise one or more haloalkylsilanes, these preferably comprise dichlorodimethylsilane and/or dichlorodiethylsilane, and more preferably dichlorodimethylsilane, wherein it is even more preferred that the one or more haloalkylsilanes preferably contained among the one or more silylating agents are dichlorodimethylsilane and/or dichlorodiethylsilane, and even more preferably wherein dichlorodimethylsilane is preferably the dihalodialkylsilane used as silylating agent in step (II).

With respect to the alkyldisilazanes which are preferably comprised among the one or more silylating agents used in step (II), any conceivable type or number of alkyldisilazanes may be employed provided that at least a portion of the catalyst provided in step (I) may be silylated therewith. Thus, as regards the one or more alkyl groups of the alkyldisilazanes preferably employed in the inventive process, no particular restriction applies, neither with respect to the number of alkyl groups nor with respect to the type of alkyl group which may be contained therein. Thus, independently from one another, the seven substituents of the alkyldisilazane structure may or may not be substituted with alkyl, provided that at least one substituent is an alkyl group, wherein preferably at least one of the silane moieties is substituted with an alkyl group. According to the present invention it is however preferred that the one or more silylating agents comprise one or more hexaalkyldisilazanes, wherein each of the silane moieties is respectively substituted by three alkyl groups. As regards the alkyl moieties present in the alkyldisilazanes and in particular in the preferred hexaalkyldisilazanes contained in the one or more silylating agents of step (II), said alkyl groups may independently from one another be branched or unbranched and/or substituted or unsubstituted. As regards the chain length of the alkyl groups, again no particular restriction applies, such that the alkyl groups may independently from one another be selected from the group consisting of optionally branched and/or optionally substituted (C1-C6) alkyl, wherein preferably the one or more alkyl groups are selected from the group consisting of optionally branched and/or optionally substituted (C1-C5)alkyl, more preferably (C1-C4)alkyl, and more preferably from the group consisting of optionally branched and/or optionally substituted (C1-C3) alkyl. According to the present invention it is however preferred that the alkyl groups are non-substituted alkyl groups, and more preferably that the alkyl groups are unbranched and unsubstituted, such that according to the invention it is particularly preferred that the alkyl groups are, independently from one another, selected from the group consisting of methyl, ethyl, or propyl, wherein even more preferably the alkyl groups are selected from ethyl and methyl. Thus, according to the present invention it is particularly preferred that the one or more silylating agents in step (II) comprise hexamethyldisilazane and/or hexaethyldisilazane, and preferably hexamethyldisilazane, wherein even more preferably hexamethyldisilazane and hexaethyldisilazane, preferably hexamethyldisilazane is employed as the one or more silylating agents in step (II) of the inventive process.

Concerning the conditions under which the treating of the catalyst in step (II) is performed, no particular restrictions apply relative to the temperature, pressure, or other reaction parameters such as in particular the atmosphere under which said step is performed provided that at least a portion of the catalyst provided in step (I) may be silylated. Thus, as regards the temperature at which the catalyst is treated in step (II), any suitable temperature may be employed. Thus, by way of example, step (II) may be conducted under heating, wherein preferably heating is conducted at a temperature ranging from 40 to 150° C., and more preferably at a temperature ranging from 50 to 130° C., more preferably from 60 to 110° C., more preferably from 70 to 100° C., and even more preferably from 75 to 95° C. According to the invention it is particularly preferred that the silylation in step (II) is conducted at a temperature ranging from 80 to 90° C.

Regarding the atmosphere under which the silylation in step (II) of the inventive process is conducted, any suitable atmosphere may be employed provided that at least a portion of the catalyst provided in step (I) may be silylated in step (II). According to particular and preferred embodiments of the inventive process wherein silylating agents are employed which are air sensitive, it is accordingly preferred that silylation in step (II) is performed in an inert atmosphere such as in an atmosphere containing one or more noble gases and/or nitrogen, including combinations of two or more thereof, preferably in an atmosphere containing argon and/or nitrogen, wherein even more preferably step (II) is conducted in a nitrogen atmosphere.

Regarding the apparatus in which the silylation in step (II) of the inventive process may be conducted, no particular restriction applies such that in principle any suitable apparatus may be employed provided that at least a portion of the catalyst provided in step (I) may be effectively silylated. According to the inventive process it is however preferred that the silylation in step (II) is conducted in a reactor, in particular in cases in which the catalyst is heated in step (II) for the silylation treatment. As regards the types of reactors which may preferably be used to this effect, again no restriction applies, such that a fixed bed as well as a fluidized bed reactor may be employed to this effect. According to the inventive process it is however particularly preferred that the silylation in step (II) is conducted in a fixed bed reactor.

In addition to a catalyst for the conversion of oxygenates to olefins according to the present invention as described in the present application, and especially according to the particular and preferred embodiments thereof, the present invention likewise relates to those catalysts for the conversion of oxygenates to olefins which are obtainable by the preparation process according to the invention, i.e. including catalysts per se which can, for example, be obtained by the preparation process according to the invention, without necessarily having to be prepared by this process. More particularly, the present invention thus relates to catalysts for the conversion of oxygenates to olefins which can be prepared by the process according to the invention, especially according to the particular and preferred embodiments thereof described in the present application, but can be or have been prepared by another process suitable for this purpose.

Thus, according to the present invention, preference is given to embodiments of the catalyst for the conversion of oxygenates to olefins in which the catalyst, and especially the catalyst according to one of the particular or preferred embodiments of the present invention, is obtainable by the process according to the invention for preparing a catalyst, preferably by one of the particular or preferred embodiments of the process according to the invention.

In addition to a catalyst for the conversion of oxygenates to olefins and a process for preparing such a catalyst, the present invention also relates to a process for converting oxygenates to olefins. More particularly, the present invention relates to such a process comprising:

(1) providing a gas stream comprising one or more oxygenates;
(2) contacting the gas stream with a catalyst according to the present invention.

With regard to the catalyst which can be used in the process according to the invention for converting oxygenates to olefins, there is in principle no restriction whatsoever, provided that it is a catalyst according to the present invention as obtainable, for example, also by the process according to the invention, and provided that this catalyst is suitable for the conversion of at least one oxygenate to at least one olefin. This is especially true of the embodiments of the inventive catalyst according to the particular and preferred embodiments of the present invention.

The same applies correspondingly to the one or more oxygenate(s) present in the gas stream according to (1), and so there is no restriction here whatsoever in principle in the process according to the invention, provided that the one or more oxygenates present in the gas stream according to (1) can be converted by one of the catalysts according to the present invention and especially according to the particular and preferred embodiments thereof to at least one olefin when contacted according to (2). According to the present invention, however, it is preferable that the one or more oxygenates present in the gas stream according to (1) are selected from the group consisting of aliphatic alcohols, ethers, carbonyl compounds and mixtures of two or more thereof. Further preferably, the one or more oxygenates are selected from the group consisting of ($C_1$-$C_6$)-alcohols, di($C_1$-$C_3$)alkyl ethers, ($C_1$-$C_6$)-aldehydes, ($C_2$-$C_6$)-ketones and mixtures of two or more thereof, further preferably consisting of ($C_1$-$C_4$)-alcohols, di($C_1$-$C_2$)alkyl ethers, ($C_1$-$C_4$)-aldehydes, ($C_2$-$C_4$)-ketones and mixtures of two or more thereof. In yet further preferred embodiments of the present invention, the gas stream according to (1) comprises one or more oxygenates selected from the group consisting of methanol, ethanol, n-propanol, isopropanol, butanol, dimethyl ether, diethyl ether, ethyl methyl ether, diisopropyl ether, di-n-propyl ether, formaldehyde, dimethyl ketone and mixtures of two or more thereof, the one or more oxygenates further preferably being selected from the group consisting of methanol, ethanol, dimethyl ether, diethyl ether, ethyl methyl ether and mixtures of two or more thereof. In particularly preferred embodiments of the process according to the invention for converting oxygenates to olefins, the gas stream according to (1) comprises methanol and/or dimethyl ether as the one or more oxygenates, and dimethyl ether is more preferably the oxygenate present in the gas stream according to (1).

Thus, according to the present invention, preference is given to embodiments of the process for converting oxygenates to olefins in which the gas stream according to (1) comprises one or more oxygenates selected from the group consisting of aliphatic alcohols, ethers, carbonyl compounds and mixtures of two or more thereof, preferably consisting of ($C_1$-$C_6$) alcohols, di($C_1$-$C_3$)alkyl ethers, ($C_1$-$C_6$) aldehydes, ($C_2$-$C_6$) ketones and mixtures of two or more thereof, further preferably consisting of ($C_1$-$C_4$) alcohols, di($C_1$-$C_2$) alkyl ethers, ($C_1$-$C_4$) aldehydes, ($C_2$-$C_4$) ketones and mixtures of two or more thereof, further preferably from the group consisting of methanol, ethanol, n-propanol, isopropanol, butanol, dimethyl ether, diethyl ether, ethyl methyl ether, diisopropyl ether, di-n-propyl ether, formaldehyde, dimethyl ketone and mixtures of two or more thereof, further preferably from the group consisting of methanol, ethanol, dimethyl ether, diethyl ether, ethyl methyl ether and mixtures of two or more thereof, the gas stream further preferably comprising methanol and/or dimethyl ether, and more preferably dimethyl ether.

On the other hand, with regard to the content of oxygenates in the gas stream according to (1) to the process according to the invention for converting oxygenates to olefins, there is no restriction whatsoever according to the present invention here either, provided that, when the gas stream is contacted in (2) with a catalyst according to the present invention, at least one oxygenate can be converted to at least one olefin. In preferred embodiments, the content of oxygenates in the gas stream according to (1) is in the range from 5 to 100% by volume based on the total volume, the content especially being based on a gas stream at a temperature in the range from 200 to 700° C. and at a pressure of 101.3 kPa, preferably at a temperature in the range from 250 to 650° C., further preferably from of 300 to 600° C., further preferably from 350 to 560° C., further preferably from 400 to 540° C., further preferably from 430 to 520° C., and further preferably in the range from 450 to 500° C. and at a pressure of 101.3 kPa. According to the present invention, it is further preferred that the content of oxygenates in the gas stream according to (1) is in the range from 10 to 99% by volume, further preferably from 15 to 95% by volume, further preferably from 20 to 90% by volume, further preferably from 25 to 80% by volume, further preferably from 30 to 70% by volume, further preferably from 30 to 60% by volume and further preferably from 30 to 50% by volume. In particularly preferred embodiments of the process according to the invention for converting oxygenates to olefins, the content of oxygenates in the gas stream according to (1) is in the range from 30 to 45% by volume.

Thus, according to the present invention, preference is given to embodiments of the process for converting oxygenates to olefins in which the content of oxygenates in the gas stream according to (1) is in the range from 5 to 100% by volume based on the total volume, preferably from 10 to 99% by volume, further preferably from 15 to 95% by volume, further preferably from 20 to 90% by volume, further preferably from 25 to 80% by volume, further preferably from 30 to 70% by volume, further preferably from 30 to 60% by volume, further preferably from 30 to 50% by volume, and further preferably from 30 to 45% by volume.

With regard to the other components in the gas stream according to (1) in the process according to the invention, there is in principle no restriction whatsoever, provided that the gas stream is suitable overall for converting at least one of the oxygenates to at least one olefin in step (2) when contacted with a catalyst according to the present invention. In addition, for example, as well as the one or more oxygenates in the gas stream according to (1), one or more inert gases may also be present therein, for example one or more noble gases, nitrogen, carbon monoxide, carbon dioxide, water and mixtures of two or more thereof. In particular embodiments of the present invention, the gas stream according to (1) of the process according to the invention, as well as the one or more oxygenates, comprises water.

With regard to those preferred embodiments in which, as well as the one or more oxygenates, water is present in the gas stream according to (1), there is no restriction in principle with respect to the water content which may be present therein, provided that the conversion of at least one oxygenate in the gas stream to at least one olefin in step (2) of the contacting of the gas stream can be effected with a catalyst according to the present invention. In these preferred embodiments, however, it is preferable that the water content in the gas stream is in the range from 5 to 60% by volume based on the total volume, the water content more preferably being in the range from 10 to 55% by volume, further preferably from 20 to 50% by volume and further preferably from 30 to 45% by volume.

Thus, according to the present invention, preference is given to embodiments of the process for converting oxygenates to olefins in which water is present in the gas stream according to (1), preferably in the range from 5 to 60% by volume based on the total volume, preferably from 10 to 55% by volume, further preferably from 20 to 50% by volume, and further preferably from 30 to 45% by volume.

In particularly preferred embodiments of the process according to the invention for converting oxygenates to olefins, the gas stream provided in (1) originates from a preliminary reaction, preferably from the conversion of one or more alcohols to one or more ethers, especially from the conversion of one or more alcohols selected from the group consisting of methanol, ethanol, n-propanol, isopropanol and mixtures of two or more thereof, further preferably from the group consisting of methanol, ethanol, n-propanol and mixtures of two or more thereof, the gas stream provided in (1) more preferably originating from a preliminary reaction of methanol and/or ethanol and methanol further preferably being at least partly converted to one or more di($C_1$-$C_2$)alkyl ethers, preferably to one or more di($C_1$-$C_2$)alkyl ethers selected from the group consisting of dimethyl ether, diethyl ether, ethyl methyl ether and mixtures of two or more thereof. For instance, the gas stream provided in (1), in a particularly preferred embodiment, originates from a preliminary reaction of conversion of methanol to dimethyl ether.

In the particularly preferred embodiments of the process according to the invention in which the gas stream provided in (1) originates from a preliminary reaction of one or more alcohols, there is no particular restriction whatsoever in principle with respect to the reaction and hence the reaction product of the conversion of one or more alcohols, provided that this leads to a gas stream comprising one or more oxygenates which, when contacted in (2) with a catalyst according to the present invention, enables the conversion of at least one of the oxygenates to at least one olefin. In these particular embodiments, it is further preferable that the preliminary reaction leads to conversion of at least one alcohol to at least one ether and especially to at least one dialkyl ether, the preliminary reaction more preferably being a dehydration in which water is obtained as a coproduct to one or more dialkyl ethers. In the particular and preferred embodiments of the present invention in which the gas stream provided in (1) originates from a preliminary reaction, it is particularly preferred in the process according to the invention that such a gas stream originating from a preliminary reaction is supplied directly and without workup to the process according to the invention in step (1).

With respect to the manner of contacting the gas stream with a catalyst according to the present invention in step (2) of the process according to the invention for converting oxygenates to olefins, there is in principle no restriction whatsoever, provided that the conversion of at least one oxygenate to at least one olefin can be implemented. This applies, for example, to the temperature at which the contacting (2) takes place. Thus, for example, the contacting in step (2) of the process according to the invention can take place at a temperature in the range from 200 to 700° C., preference being given to selecting temperatures in the range from 250 to 650° C., further preferably from 300 to 600° C., further preferably from 350 to 560° C., further preferably from 400 to 540° C. and further preferably from 430 to 520° C. In particularly preferred embodiments of the present invention, the contacting according to (2) of the process according to the invention is performed at a temperature in the range from 450 to 500° C.

Thus, according to the present invention, preference is given to embodiments of the process for converting oxygenates to olefins in which the contacting according to (2) is effected at a temperature in the range from 200 to 700° C., preferably from 250 to 650° C., further preferably from 300 to 600° C., further preferably from 350 to 560° C., further preferably from 400 to 540° C., further preferably from 430 to 520° C., and further preferably from 450 to 500° C.

The same applies correspondingly to the pressure at which the gas stream is contacted in step (2) of the process according to the invention with the catalyst according to the present invention. Thus, the contacting can in principle take place at any desired pressure, provided that this allows the conversion of at least one oxygenate to at least one olefin by virtue of the contacting of the gas stream with the catalyst. Thus, the pressure, for example in the contacting in step (2), may be in the range from 0.1 to 10 bar, the pressure according to the present application indicating the absolute pressure, such that a pressure of 1 bar in the contacting accordingly corresponds to the standard pressure of 1.03 kPa. According to the present invention, the contacting in step (2) takes place preferably at a pressure from 0.3 to 7 bar, further preferably from 0.5 to 5 bar, further preferably from 0.7 to 3 bar, further preferably from 0.8 to 2.5 bar and further preferably from 0.9 to 2.2 bar. In particularly preferred embodiments of the process according to the invention for converting oxygenates to olefins, the contacting in step (2) takes place at a pressure of 1 to 2 bar.

Thus, according to the present invention, preference is given to embodiments of the process for converting oxygenates to olefins in which the contacting according to (2) is effected at a pressure in the range from 0.1 to 10 bar, preferably from 0.3 to 7 bar, further preferably from 0.5 to 5 bar, further preferably from 0.7 to 3 bar, further preferably from 0.8 to 2.5 bar, further preferably from 0.9 to 2.2 bar, and further preferably from 1 to 2 bar.

In addition, there are no particular restrictions with respect to the manner of performance of the process according to the invention for converting oxygenates to olefins, and so it is possible to use either a continuous or a noncontinuous process, the noncontinuous process being performable, for example, in the form of a batch process. According to the present invention, however, it is preferable to conduct the process according to the invention for the conversion of oxygenates as a continuous process. Thus, according to the present invention, preference is given to embodiments of the process for converting oxygenates to olefins in which the process is a continuous process.

With respect to these preferred embodiments of a continuous process, there are no restrictions whatsoever with respect to the space velocity selected, provided that the conversion of an oxygenate to an olefin can be effected. Thus, it is possible to select, for example, space velocities (WHSV=weight hourly space velocity is calculated as the ratio of oxygenate reactant stream in kg/h to the amount of zeolite in the reactor in kg) in the contacting in step (2) which are in the range from 0.5 to 50 $h^{-1}$, preference being given to selecting space velocities from 1 to 30 $h^{-1}$, further preferably from 2 to 20 $h^{-1}$, further preferably from 3 to 15 $h^{-1}$ and further preferably from 4 to 10 $h^{-1}$. In particularly preferred embodiments of the process according to the invention for converting oxygenates, space velocities for the contacting of the gas stream in step (2) in the range from 5 to 7 $h^{-1}$ are selected.

With respect to the preferred space velocities according to the particular embodiments of the process according to the invention for converting oxygenates to olefins, these are preferably established in connection with a conversion of oxygenates within a particular range. Thus, the space velocities according to the particular and preferred embodiments of the process according to the invention may be established at a conversion of oxygenate in the range from, for example, 50 to 99.9%. According to the present invention, the space velocity according to the particular and preferred embodiments, however, is preferably established at a conversion of oxygenates in the range from 70 to 99.5%, further preferably from 90 to 99%, further preferably from 95 to 98.5%, further preferably from 96 to 98% and further preferably 96.5 to 97.5%. According to the present invention, however, it is further preferred that the space velocity in the course of contacting of the gas stream in step (2) of the process according to the invention is established at a full conversion from 96.5 to 99.9% or more of the oxygenate, further preferably from 97.5 to 99.9% or more, further preferably from 98 to 99.9% or more, further preferably from 99 to 99.9% or more and further preferably from 99.5 to 99.9% or more conversion of oxygenates.

Thus, according to the present invention, preference is given to embodiments of the process for converting oxygenates to olefins in which the space velocity in the course of contacting according to (2) is in the range from 0.5 to 50 $h^{-1}$, preferably from 1 to 30 $h^{-1}$, further preferably from 2 to 20 $h^{-1}$, further preferably from 3 to 15 $h^{-1}$, further preferably from 4 to 10 $h^{-1}$ and further preferably from 5 to 7 $h^{-1}$.

As described above and shown in the examples of the present application, it is possible to achieve particularly long service lives with the inventive catalyst in a process for converting oxygenates as described in the present application, especially with respect to the particular and preferred embodiments of the process according to the invention. It has thus been found that, surprisingly, the use of a catalyst according to the present invention can considerably increase the service life of the catalyst before the process has to be interrupted for regeneration of the catalyst, at least with respect to the use of this catalyst batch compared to the use of catalysts according to the prior art. It is thus particularly preferable according to the present invention to select long service lives for the performance of the process for converting oxygenates to olefins at one of the particular or preferred space velocities, as described in the present application.

Thus, preference is given to service lives in the range from 50 to 450 h, further preferably in the range from 100 to 400 h, further preferably from 150 to 375 h, further preferably from 200 to 350 h, further preferably from 225 to 325 h and further preferably from 250 to 310 h. More particularly, based on the particular and preferred space velocities at which the process according to the invention is performed, preference is thus given, for example, to service lives of 50 to 450 h at a space velocity in the range from 0.5 to 50 $h^{-1}$. Further preference is given to a service life of 100 to 400 h at a space velocity in the range from 1 to 30 $h^{-1}$, further preference to a service life of 150 to 375 h at a space velocity in the range from 2 to 20 $h^{-1}$, further preference to a service life of 200 to 350 h at a space velocity in the range from 3 to 15 $h^{-1}$, and further preference to a service life of 225 to 325 h at a space velocity in the range from 4 to 10 $h^{-1}$. In a particularly preferred embodiment of the process according to the invention, a service life of the catalyst, during which the continuous process is performed without interruption, in the range from 250 to 310 h at a space velocity of 5 to 7 $h^{-1}$ is selected. As already above with respect to the particular and preferred space velocities which are selected in the process according to the invention, the particular and preferred embodiments with respect to the selected service life and especially the selected service lives in combination with particular space velocities relate to a simultaneous full conversion of the catalyst and especially to conversions in the range from 96.5 to 99.9% or more, preferably from 97.5 to 99.9% or more, further preferably from 98 to 99.9% or more, further preferably from 99 to 99.9% or more and further preferably from 99.5 to 99.9% or more with respect to the conversion of the one or more oxygenates present in the gas stream according to (1) of the process according to the invention.

Thus, according to the present invention, further preference is given to embodiments of the process for converting oxygenates to olefins in which the service life of the catalyst during which the continuous process is performed without interruption is in the range from 50 to 450 h, preferably from 100 to 400 h, more preferably from 150 to 375 h, more preferably from 200 to 350 h, more preferably from 225 to 325 h, and more preferably from 250 to 310 h.

The present invention further also relates to the use of the inventive catalyst as described above, and especially to the use of the inventive catalyst according to the particular and preferred embodiments as described in the present application. According to the present invention, there is no restriction whatsoever in principle with respect to the use of the inventive catalyst, and so it can be used either for the conversion of oxygenates to olefins or in any conceivable catalytic process in which the catalyst exhibits a corresponding catalytic action with respect to a chemical conversion. According to the present invention, however, the inventive catalyst is preferably used in a methanol-to-olefin process (MTO process), in a dimethylether to olefin process (DTO process), methanol-to-gasoline process (MTG process), in a methanol-to-hydrocarbon process, in a biomass to olefins and/or biomass to aromatics process, in a methane to benzene process, for alkylation of aromatics or in fluid catalytic cracking processes (FCC processes), and preferably in a methanol-to-olefin process (MTO process) and/or in a dimethylether to olefin process (DTO process). According to the present invention it is particularly preferred that the inventive catalyst according to any one of the particular and preferred embodiments as described in the present application is used in a methanol-to-propylene process (MTP process), in a methanol-to-propylene/butylene process (MT3/4 process), in a dimethylether-to-propylene process (DTP process), in a dimethylether-to-propylene/butylene process (DT3/4 process), and/or in a dimethylether-to-ethylene/propylene (DT2/3 process).

The present invention includes the following embodiments, wherein these include the specific combinations of embodiments as indicated by the respective interdependencies defined therein:

1. A catalyst for the conversion of oxygenates to olefins, wherein the catalyst comprises one or more zeolites of the MFI, MEL and/or MWW structure type and particles of one or more metal oxides,
   the one or more zeolites of the MFI, MEL and/or MWW structure type comprising one or more alkaline earth metals selected from the group consisting of Mg, Ca, Sr, Ba and combinations of two or more thereof,
   wherein the catalyst displays a water uptake of 9.0 wt.-% or less, preferably of 8.0 wt.-% or less, more preferably of 7.0 wt.-% or less, more preferably of 6.0 wt.-% or less, more preferably of 5.5 wt.-% or less, wherein more preferably the catalyst displays a water uptake ranging from 0.5 to 5.0 wt.-%, more preferably of 1.0 to 4.5 wt.-%, more preferably of 1.5 to 4.0 wt.-%, more preferably of 2.0 to 3.5 wt.-%, and more preferably of 2.5 to 3.0 wt.-%.
2. The catalyst of embodiment 1, wherein the particles of the one or more metal oxides comprise phosphorus, the phosphorus being present at least partly in oxidic form.
3. The catalyst of embodiment 1 or 2, wherein the one or more zeolites of the MFI, MEL and/or MWW structure type comprise phosphorus, the phosphorus being present at least partly in oxidic form.
4. The catalyst of any of embodiments 1 to 3, wherein the one or more zeolites are of the MFI structure type, wherein preferably the one or more zeolites of the MFI structure type are selected from the group consisting of ZSM-5, ZBM-10, [As—Si—O]-MFI, [Fe—Si—O]-MFI, [Ga—Si—O]-MFI, AMS-1B, AZ-1, boron-C, boralite C, encilite, FZ-1, LZ-105, monoclinic H-ZSM-5, mutinaite, NU-4. NU-5, silicalite, TS-1, TSZ, TSZ-III, TZ-01, USC-4, USI-108, ZBH, ZKQ-1B, ZMQ-TB and mixtures of two or more thereof, further preferably from the group consisting of ZSM-5, ZBM-10 and mixtures thereof, the zeolite of the MFI structure type preferably being ZSM-5.
5. The catalyst of any of embodiments 1 to 4, wherein the alkaline earth metals are selected from the group consisting of Mg, Ca, Sr and combinations of two or more thereof, wherein preferably the alkaline earth metal is Mg.
6. The catalyst of any of embodiments 1 to 5, wherein the one or more zeolites of the MFI, MEL and/or MWW structure type comprise the one or more alkaline earth metals in a total amount in the range from 0.1 to 20% by weight, based on the total amount of the one or more zeolites of the MFI, MEL and/or MWW structure type and calculated as the metal, preferably in a total amount in the range of 0.5-15% by weight, more preferably of 1-10% by weight, more preferably of 2-7% by weight, more preferably of 3-5% by weight, more preferably of 3.5-4.5% by weight, and more preferably of 3.8-4.2% by weight.

7. The catalyst of any of embodiments 1 to 6, wherein the one or more metal oxides are selected from the group consisting of silica, alumina, titania, zirconia, aluminum-titanium mixed oxides, aluminum-zirconium mixed oxides, aluminum-lanthanum mixed oxides, aluminum-zirconium-lanthanum mixed oxides, titanium-zirconium mixed oxides and mixtures of two or more thereof, preferably from the group consisting of silica, alumina, aluminum-titanium mixed oxides, aluminum-zirconium mixed oxides, aluminum-lanthanum mixed oxides, aluminum-zirconium-lanthanum mixed oxides and mixtures of two or more thereof, wherein more preferably the metal oxide is alumina.

8. The catalyst of any of embodiments 1 to 7, wherein the zeolite:metal oxide weight ratio in the catalyst is in the range from 10:90 to 95:5, preferably in the range from 20:80 to 90:10, more preferably in the range from 40:60 to 80:20, more preferably in the range from 45:55 to 70:30, more preferably of from 50:50 to 75:25, and more preferably in the range from 55:45 to 65:35.

9. The catalyst of any of embodiments 2 to 8, wherein the total amount of phosphorus, based on the sum of the total weight of zeolites of the MFI, MEL and/or MWW structure type and the total weight of the particles of the one or more metal oxides and calculated as the element, is in the range from 0.1 to 20% by weight, preferably from 0.5 to 15% by weight, more preferably from 1 to 10% by weight, more preferably from 2 to 7% by weight, more preferably from 2.5 to 5% by weight, more preferably from 3 to 4.5% by weight, more preferably from 3.3 to 4.2% by weight, more preferably from 3.5 to 4% by weight, and more preferably in the range from 3.6 to 3.8% by weight.

10. The catalyst of any of embodiments 1 to 9 in the form of a shaped body comprising a mixture of the one or more zeolites of the MFI, MEL and/or MWW structure type and of the particles of the one or more metal oxides.

11. A process for preparing a catalyst according to any of embodiments 1 to 10, comprising
(I) providing a catalyst comprising one or more zeolites of the MFI, MEL and/or MWW structure type and particles of one or more metal oxides,
the one or more zeolites of the MFI, MEL and/or MWW structure type comprising one or more alkaline earth metals selected from the group consisting of Mg, Ca, Sr, Ba and combinations of two or more thereof; and
(II) treating the catalyst with one or more silylating agents;
(III) optionally calcining the silylated catalyst obtained in (II), 12. The process of embodiment 11, wherein step (I) comprises
(I.a) providing one or more zeolites of the MFI, MEL and/or MWW structure type;
(I.b) impregnating the one or more zeolites of the MFI, MEL and/or MWW structure type with a solution comprising the one or more alkaline earth metals, preferably by means of spray impregnation;
(I.c) optionally drying the one or more impregnated zeolites obtained in (I.b);
(I.d) optionally calcining the one or more impregnated zeolites obtained in (I.b) or (I.c);
(I.e) preparing a mixture comprising the one or more impregnated and optionally dried and/or calcined zeolites of the MFI, MEL and/or MWW structure type, one or more solvents and particles of the one or more metal oxides and/or precursor compounds of the one or more particles of the one or more metal oxides;
(I.f) homogenizing the mixture obtained in (I.e);
(I.g) extruding the homogenized mixture obtained in (I.f);
(I.h) optionally drying the extrudate obtained in (I.g);
(I.i) optionally calcining the extrudate obtained in (I.g) or (I.h).

13. The process of embodiment 12, wherein step (I.e) comprises
(I.e.1) preparing a mixture comprising the one or more impregnated and optionally dried and/or calcined zeolites of the MFI, MEL and/or MWW structure type and particles of the one or more metal oxides and/or precursor compounds of the one or more particles of the one or more metal oxides:
(I.e.2) admixing the mixture obtained in (I.e1) with a phosphorus-comprising solution, preferably with phosphoric acid;
(I.e.3) mixing the mixture obtained in (I.e.2) with one or more solvents.

14. The process of embodiment 12 or 13, wherein step (I) further comprises
(I.j) impregnating the optionally dried and/or calcined extrudate with a phosphorus-comprising solution, preferably with phosphoric acid;
(I.k) optionally drying the impregnated extrudate obtained in (I.j);
(I.l) optionally calcining the extrudate obtained in (I.j) or (I.k).

15. The process of any of embodiments 12 to 14, wherein the impregnating in (I.b) or the drying in (I.c) or the calcining in (I.d) is followed by bringing the one or more impregnated zeolites of the MFI, MEL and/or MWW structure type to a particle size $D_{50}$ in the range from 5 to 1000 μm, preferably from 10 to 750 μm, more preferably from 30 to 500 μm, more preferably from 50 to 300 μm, more preferably from 70 to 200 μm, more preferably from 80 to 150 μm, and more preferably from 90 to 120 μm, preferably by milling.

16. The process of any of embodiments 12 to 15, wherein the drying in (I.c), (I.h) and/or (I.k) is effected at a temperature in the range from 50 to 220° C., preferably from 70 to 180° C., more preferably from 80 to 150° C., more preferably from 90 to 130° C., more preferably from 100 to 125° C., and more preferably from 110 to 120° C.

17. The process of any of embodiments 11 to 16, wherein the calcining in (I.d), (I.i), (I.l) and/or (III) is effected at a temperature in the range from 300 to 850° C., preferably from 350 to 750° C., more preferably from 400 to 700° C., more preferably from 450 to 650° C., more preferably from 480 to 600° C., and more preferably from 500 to 550° C.

18. The process of any of embodiments 12 to 17, wherein the solution used in (I.b) and/or (I.j) or (I.e.2) and/or the mixture prepared in (I.e) or (I.e.3) comprises one or more solvents selected from the group consisting of alcohols, water, mixtures of two or more alcohols, and mixtures of water and one or more alcohols, preferably from the group consisting of $(C_1-C_6)$ alcohols, water, mixtures of two or more $(C_1-C_6)$ alcohols, and mixtures of water and one or more $(C_1-C_6)$ alcohols, more preferably $(C_1-C_4)$ alcohols, water, mixtures of two or more $(C_1-C_4)$ alcohols, and mixtures of water and one or more $(C_1-C_4)$ alcohols, more preferably consisting of methanol, ethanol, n-propanol, isopropanol, water and mixtures of two or more thereof, more preferably consisting of methanol, ethanol, water and mixtures of two or more thereof, the solvent more preferably being water, preferably distilled water.

19. The process of any of embodiments 11 to 18, wherein the one or more silylating agents are selected from the group consisting of alkyldisilazanes, alkylalkoxysilanes, haloalkylsilanes, and mixtures of two or more thereof, wherein the one or more silylating agents preferably comprise one or more alkyldisilazanes.

20. The process of embodiment 19, wherein the alkyldisilazanes are selected from the group consisting of hexaalkyldisilazanes, wherein independently form one another the alkyl groups are preferably selected from the group consisting of optionally branched and/or optionally substituted (C1-C6)alkyl, preferably (C1-C5)alkyl, more preferably (C1-C4)alkyl, and more preferably optionally branched and/or optionally substituted (C1-C3)alkyl, wherein more preferably the alkyl groups are, independently from one another, selected from the group consisting of optionally substituted methyl, ethyl, or propyl, wherein more preferably the alkyl groups are selected from ethyl and methyl, wherein even more preferably the alkyldisilazane is hexamethyldisilazane and/or hexaethyldisilazane, preferably hexamethyldisilazane.

21. The process of embodiment 19 or 20, wherein the alkylalkoxysilanes are selected from the group consisting of trialkylalkoxysilanes, alkyltrialkoxysilanes, and mixtures of two or more thereof, wherein independently from one another the alkyl chains of the trialkylalkoxysilanes and alkyltrialkoxysilanes are preferably selected from the group consisting of optionally branched and/or optionally substituted (C1-C6)alkyl, preferably (C1-C5)alkyl, more preferably (C1-C4) alkyl, and more preferably optionally branched and/or optionally substituted (C1-C3)alkyl, wherein more preferably the alkyl groups are, independently from one another, selected from the group consisting of optionally substituted methyl, ethyl, or propyl, wherein more preferably the alkyl groups are selected from ethyl and methyl, wherein even more preferably the alkylalkoxysilane is selected from the group consisting of methoxytrimethylsilane, ethoxytrimethylsilane, propoxytrimethylsilane, methyltrimethoxysilane, methyltriethoxysilane, ethyltrimethoxysilane, ethyltriethoxysilane, propyltrimethoxysilane, propyltriethoxysilane, and mixtures of two or more thereof, more preferably from the group consisting of methoxytrimethylsilane, ethoxytrimethylsilane, methyltrimethoxysilane, methyltriethoxysilane, ethyltrimethoxysilane, ethyltriethoxysilane, and mixtures of two or more thereof.

22. The process of any one of embodiments 19 to 21, wherein the haloalkylsilanes are selected from the group consisting of dihalodialkylsilanes, wherein independently from one another the alkyl chains of the dihalodialkylsilanes are preferably selected from the group consisting of optionally branched and/or optionally substituted (C1-C6)alkyl, preferably (C1-5)alkyl, more preferably (C1-C4)alkyl, and more preferably optionally branched and/or optionally substituted (C1-C3)alkyl, wherein more preferably the alkyl groups are, independently from one another, selected from the group consisting of optionally substituted methyl, ethyl, or propyl, wherein more preferably the alkyl groups are selected from ethyl and methyl, and
    wherein independently from one another the halo groups are selected from the group consisting of halogens and pseudohalogens, preferably from the group consisting of CN, F, Cl, Br, and I, more preferably from the group consisting of CN, Cl, and Br, wherein more preferably the halo groups are, independently from one another Cl or Br, preferably Cl, and
    wherein the haloalkylsilane is preferably dichlorodimethylsilane and/or dichlorodiethylsilane, preferably dichlorodimethylsilane.

23. The process of any one of embodiments 11 to 22, wherein step (II) is conducted under heating, preferably at a temperature ranging from 40 to 150° C., more preferably from 50 to 130° C., more preferably from 60 to 110° C., more preferably from 70 to 100° C., more preferably from 75 to 95° C., and more preferably from 80 to 90° C.

24. A catalyst for the conversion of oxygenates to olefins, obtainable by a process according to any of embodiments 11 to 23.

25. A process for converting oxygenates to olefins, comprising:
    (1) providing a gas stream comprising one or more oxygenates;
    (2) contacting the gas stream with a catalyst according to any of embodiments 1 to 10 and 24.

26. The process of embodiment 25, wherein the gas stream according to (1) comprises one or more oxygenates selected from the group consisting of aliphatic alcohols, ethers, carbonyl compounds and mixtures of two or more thereof, preferably from the group consisting of $(C_1-C_6)$ alcohols, di$(C_1-C_3)$alkyl ethers, $(C_1-C_6)$ aldehydes, $(C_2-C_6)$ ketones and mixtures of two or more thereof, more preferably consisting of $(C_1-C_4)$ alcohols, di$(C_1-C_2)$alkyl ethers, $(C_1-C_4)$ aldehydes, $(C_2-C_4)$ ketones and mixtures of two or more thereof, more preferably from the group consisting of methanol, ethanol, n-propanol, isopropanol, butanol, dimethyl ether, diethyl ether, ethyl methyl ether, diisopropyl ether, di-n-propyl ether, formaldehyde, dimethyl ketone and mixtures of two or more thereof, more preferably from the group consisting of methanol, ethanol, dimethyl ether, diethyl ether, ethyl methyl ether and mixtures of two or more thereof, the gas stream more preferably comprising methanol and/or dimethyl ether, and more preferably dimethyl ether.

27. The process of embodiment 25 or 26, wherein the content of oxygenates in the gas stream according to (1) is in the range from 5 to 100% by volume based on the total volume, preferably from 10 to 99% by volume, more preferably from 15 to 95% by volume, more preferably from 20 to 90% by volume, more preferably from 25 to 80% by volume, more preferably from 30 to 70% by volume, more preferably from 30 to 60% by volume, more preferably from 30 to 50% by volume, and more preferably from 30 to 45% by volume.
28. The process of any of embodiments 25 to 27, wherein the water content in the gas stream according to (1) is in the range from 5 to 60% by volume based on the total volume, preferably from 10 to 55% by volume, more preferably from 20 to 50% by volume, and more preferably from 30 to 45% by volume.
29. The process of any of embodiments 25 to 28, wherein the contacting according to (2) is effected at a temperature in the range from 200 to 700° C., preferably from 250 to 650° C., more preferably from 300 to 600° C., more preferably from 350 to 560° C., more preferably from 400 to 540° C., more preferably from 430 to 520° C., and more preferably from 450 to 500° C.
30. The process of any of embodiments 25 to 29, wherein the contacting according to (2) is effected at a pressure in the range from 0.1 to 10 bar, preferably from 0.3 to 7 bar, more preferably from 0.5 to 5 bar, more preferably from 0.7 to 3 bar, more preferably from 0.8 to 2.5 bar, more preferably from 0.9 to 2.2 bar, and more preferably from 1 to 2 bar.
31. The process of any of embodiments 25 to 30, wherein the process is a continuous process.
32. The process of embodiment 31, in which the space velocity in the contacting according to (2) is in the range from 0.5 to 50 $h^{-1}$, preferably from 1 to 30 $h^{-1}$, more preferably from 2 to 20 $h^{-1}$, more preferably from 3 to 15 $h^{-1}$, more preferably from 4 to 10 $h^{-1}$ and more preferably from 5 to 7 $h^{-1}$.
33. The process of embodiment 32, in which the service life of the catalyst during which the continuous process is performed without interruption is in the range from 50 to 450 h, preferably from 100 to 400 h, more preferably from 150 to 375 h, more preferably from 200 to 350 h, more preferably from 225 to 325 h, and more preferably from 250 to 310 h,
34. The use of a catalyst according to any of embodiments 1 to 10 and 24 in the conversion of oxygenates to olefins, in a methanol-to-olefin process (MTO process), in a dimethylether to olefin process (DTO process), methanol-to-gasoline process (MTG process), in a methanol-to-hydrocarbon process, in a biomass to olefins and/or biomass to aromatics process, in a methane to benzene process, for alkylation of aromatics or in a fluid catalytic cracking process (FCC process), preferably in a methanol-to-olefin process (MTO process) and/or in a dimethylether to olefin process (DTO process), and more preferably in a methanol-to-propylene process (MTP process), in a methanol-to-propylene/butylene process (MT3/4 process), in a dimethylether-to-propylene process (DTP process), in a dimethylether-to-propylene/butylene process (DT3/4 process), and/or in a dimethylether-to-ethylene/propylene (DT2/3 process).

EXAMPLES

Water Adsorption/Desorption Measurements

Water adsorption/desorption isotherms in the present examples were performed on a VTI SA instrument from TA Instruments following a step-isotherm program. The experiment consisted of a run or a series of runs performed on a sample material that has been placed on the microbalance pan inside of the instrument. Before the measurement was started, the residual moisture of the sample was removed by heating the sample to 100° C. (heating ramp of 5° C./min) and holding it for 6 h under a nitrogen flow. After the drying program, the temperature in the cell was decreased to 25° C. and kept constant during the measurement. The microbalance was calibrated, and the weight of the dried sample was balanced (maximum mass deviation 0.01 wt.-%). Water uptake of a sample was measured as the increase in weight compared to the dry sample. First, an adsorption curve was measured by increasing the relative humidity (RH) (expressed as weight-% water in the atmosphere inside of the cell) to which the sample was exposed and measuring the water uptake by the sample as equilibrium. The RH was increased with a step of 10% from 5% to 85% and at each step the system controlled the RH and monitored the weight of the sample until reaching the equilibrium conditions after the sample and recording the weight uptake. The total adsorbed water of the sample was taken after the sample was exposed to the 85 weight-% RH. During the desorption measurement, the RH was decreased from 85 weight-% to 5 weight-% with a step of 10% and the change in the weight of the sample (water uptake) was monitored and recorded.

Reference Example 1: Synthesis of ZSM-5 Zeolite at an $SiO_2$:$Al_2O_3$ Molar Ratio of 250

Tetraethylorthosilicate (757 kg) was stirred in a vessel. Water (470 kg) and tetrapropylammonium hydroxide (40 wt % in water, 333 kg) were added. The mixture was stirred for 60 minutes during which the temperature rose to 60° C. This was due to the hydrolysis of tetraethylorthosilicate resulting in the formation of ethanol. The ethanol was removed via distillation until a sump temperature of 95° C. was reached. Thereby 832 kg of ethanol were removed from the mixture. 832 kg of water and a solution of aluminum sulfate octadecahydrate (9.4 kg) and water (20 kg) were added to the vessel. The vessel was closed and heated to 150° C.

After stirring the gel at 150° C. for 24 h the autoclave was cooled to ambient temperature and the mixture was removed. It was treated with nitric acid (10 wt % in water) until a pH value of 7.1 was reached. The resulting suspension was filtered. The filter cake was washed with water and dried (120° C.). The dry powder was ground and subsequently calcined (5 h, 500° C.).

Elemental Analysis:
Si 43.5 wt.-%
Al 0.36 wt.-%
Na <100 ppm
K <100 ppm

Thus, according to the chemical analysis, the calcined material displayed an $SiO_2$:$Al_2O_3$ molar ratio of 233.

The material displayed a BET surface area of 441 $m^2/g$. The pore volume was determined to be 0.18 $cm^3/g$ at $p/p_0$=0.301 and the median pore width to be 0.54 nm as respectively determined via Argon adsorption using the Horvath-Kawazoe method. The total intrusion volume determined according to Hg porosimetry according to DIN 66133 was 1.45 ml/g (milliliter/gram), the respective total pore area 71.3 $m^2/g$.

Temperature programmed desorption of ammonia ($NH_3$-TPD) afforded values of 0.24 mmol/g when conducted at 107° C. and of 0.12 mmol/g when conducted at 343° C.

The material had a water uptake of 7.1 wt. % at a relative humidity of 85%.

Comparative Example 1: Preparation of an Extrudate Comprising Mg-ZSM-5 ($SiO_2$:$Al_2O_3$ Molar Ratio of 250)

The ZSM-5 powder obtained from Reference Example 1 was spray impregnated with a magnesium nitrate solution. In the course of this spray impregnation, spraying was effected to 90% of the water absorption or the zeolite powder. The amount of Mg weighed in was such that the powder after the calcination comprises 4% by weight of Mg. For impregnation, 3.00 kg of zeolite powder were introduced into a tumble mixer. 1.34 kg of magnesium nitrate were dissolved in water and further diluted with a total amount of 2.6 liters of distilled water. The resulting magnesium nitrate solution was then sprayed onto the ZSM-5 powder through a glass spray nozzle while rotating over a time period of 110 min. On completion of addition of the magnesium nitrate solution, the powder was dried under vacuum (100 mbar) at 90° C. for 310 min while further rotating, calcined at 500° C. in a convection muffle furnace for 250 min, milled and sieved through a sieve having a mesh size of 1 mm.

The BET surface area of the resulting magnesium-impregnated zeolite was BET 324 $m^2/g$.

Elemental Analysis:
Mg: 4.0 g/100 g

Temperature programmed desorption of ammonia ($NH_3$-TPD) afforded values of 0.53 mmol/g when conducted at 135° C.

The Mg-ZSM-5 powder prepared by spray impregnation was further processed with pseudoboehmite (Pural SB; Sasol) as a binder to give extrudates. The starting weights were selected such that the zeolite/binder ratio in the calcined extrudate corresponds to 60:40. For this purpose, 2.52 kg of zeolite and 2.18 kg of pseudoboehmite (Pural SB; Sasol) were weighed in, mixed in a drum hoop ("Rhönrad"), admixed with dilute formic acid (65 g of formic acid in 0.5 l of distilled water) and processed with 0.125 kg of carboxymethylcellulose (Walocel; DOW) and 2.34 l of water to give a homogeneous material. The kneaded material was pressed with the aid of an extrudate press through a 2.5 mm die at 60-100 bar. Subsequently, the resulting extrudates were dried in a drying cabinet at 120° C. for 16 h and (after a heating-up period of 2 h) calcined in a muffle furnace at 500° C. for 4 h (after a heating-up period of 3 h), and the calcined extrudates were processed in a sieving machine with 2 steel balls (diameter approx. 2 cm, 258 g/ball) to give 1.6-2 mm spall.

The BET surface area of the resulting spall was 302 $m^2/g$.

Elemental Analysis:
Si: 24.1 g/100 g
Al: 20.4 g/100 g
Mg: 2.3 g/100 g

Temperature programmed desorption of ammonia ($NH_3$-TPD) afforded values of 0.61 mmol/g when conducted at 110° C.

The material had a water uptake of 7.5 wt. % at a relative humidity of 85%.

Example 1: Silylation of an Extrudate Comprising Mg-ZSM-5 ($SiO_2$:$Al_2O_3$ Molar Ratio of 250)

89 g of the spalled Mg-ZSM-5 extrudates from Comparative Example 1 were placed in a fixed bed reactor. A stream of 30 standard cubic meters of $N_2$ per hour was then directed over a saturator filled with hexamethyldisilazane (HMDS). The resulting gas mixture was then directed for 1 h into the fixed bed reactor, which was heated to 85° C.

The BET surface area of the silylated spall was 301 $m^2/g$.

Elemental Analysis:
Si: 24.7 g/100 g
Al: 19.7 g/100 g
Mg: 2.3 g/100 g

Temperature programmed desorption of ammonia ($NH_3$-TPD) afforded values of 0.54 mmol/g when conducted at 130° C.

The material had a water uptake of 3.3 wt. % at a relative humidity of 85%.

Comparative Example 2: Preparation of a Phosphorus-Treated Extrudate Comprising Mg-ZSM-5 ($SiO_2$:$Al_2O_3$ Molar Ratio of 250)

Prior to the phosphorus impregnation, the water absorption capacity of the H-ZSM-5/$Al_2O_3$ spall from Comparative Example 1 was determined to be 1 ml $H_2O$/2 g of extrudate. Accordingly, a solution of 23.3 g of 85% phosphoric acid (Sigma Aldrich) was made up to total liquid of 75 ml with distilled water. The amount of phosphoric acid was calculated such that, after the calcination, 4% by weight of phosphorus, calculated as the element, is present on the extrudate. 150 g of spall from Reference Example 2 were placed in a porcelain dish and homogenized with the dilute phosphoric acid using a spatula. The homogenized mixture was dried in a vacuum drying cabinet at 80° C. for 8 h and then calcined under air in a muffle furnace at 500° C. for 4 h (after a heating-up period of 4 h).

The BET surface area of the resulting phosphorus-impregnated spall was 236 $m^2/g$.

Elemental Analysis;
Si: 22.1 g/100 g
Al: 18.4 g/100 g
Mg: 2.1 g/100 g
P: 4.0 g/100 g Temperature programmed desorption of ammonia ($NH_3$-TPD) afforded values of 0.67 mmol/g when conducted at 127° C.

The material had a water uptake of 5.0 wt. % at a relative humidity of 85%.

Example 2: Silylation of Phosphor-Treated Extrudate Comprising Mg-ZSM-5 ($SiO_2$:$Al_2O_3$ Molar Ratio of 250)

100 g of the spalled phosphor-treated Mg-ZSM-5 extrudates from Comparative Example 2 were placed in a fixed bed reactor. A stream of 30 standard cubic meters of $N_2$ per hour was then directed over a saturator filled with hexamethyldisilazane (HMDS). The resulting gas mixture was then directed for 1 h into the fixed bed reactor, which was heated to 85° C.

70 g of the surface-passivated phosphor-treated Mg-ZSM-5 extrudates thus obtained were then heated to 500° C. in a muffle furnace over a period of 4 h and calcined at 500° C. for 4 h.

The BET surface area of the silylated spall was 221 $m^2/g$.

Elemental Analysis;
Si: 23.1 g/100 g
Al: 18.5 g/100 g
Mg: 2.2 g/100 g
P: 3.7 g/100 g Temperature programmed desorption of ammonia (NH₃-TPD) afforded values of 0.62 mmol/g when conducted at 128° C.

The material had a water uptake of 4.3 wt. % at a relative humidity of 85%.

Example 3: Regeneration of the Surface-Passivated Phosphor-Treated Mg-ZSM-5 Extrudates from Example 2

After conducting the catalyst test in Example 4 with the surface-passivated phosphor-treated Mg-ZSM-5 extrudates from Example 2, the used catalyst was extracted from the reactor and analyzed relative to its basic elements.

Elemental analysis of the used catalyst:
Si: 17.5 g/100 g
Al: 13.3 g/100 g
C: 24.8 g/100 g The used catalyst which was blackened by carbon was the regenerated by heating to 500° C. over a period of 4 h and subsequent calcination at 550° C. for 5 h. The regenerated catalyst, which regained its white appearance after the regeneration process, was again analyzed relative to its basic elements:

Elemental Analysis of the Used Catalyst:
Si: 22.4 g/100 g
Al: 18.4 g/100 g
C: <0.5 g/100 g

Example 4: Comparative Tests in the Methanol-to-Propylene/Butylene Process (DT3/4 Process)

The catalysts prepared in examples 1 and 2 (Example 3 after regeneration) and in comparative examples 1 and 2 (in each case 2 g) were respectively mixed with silicon carbide (in each case 23 g) and installed in a continuously operated, electrically heated tubular reactor. Upstream of the test reactor, methanol vapor was produced to give a gas stream comprising 75% by volume of methanol and 25% by volume of $N_2$, which was converted to dimethyl ether by means of a pre-reactor charged with 34 ml of alumina spall at 275° C. and an (absolute) pressure of 1-2 bar. The stream comprising dimethyl ether was then passed into the tubular reactor, and converted therein at a temperature of 450 to 500° C., a WHSV (=weight hourly space velocity) of 6 $h^{-1}$ based on methanol and an (absolute) pressure of 1 to 2 bar, and the reaction parameters were maintained over the entire run time. Downstream of the tubular reactor, the gaseous product mixture was analyzed by on-line chromatography.

The results achieved in the DT3/4 process for the catalysts according to examples 1, 2, and 3 (regenerated catalyst of Example 2) and according to comparative examples 1 and 2 with respect to the selectivities are shown in table 1, these reproducing the average selectivities during the run time of the catalyst in which the conversion of methanol was 97% or more.

TABLE 1

Average selectivities at a methanol conversion of >97%.

|  | Comp. Ex. 1 | Ex. 1 | Comp. Ex. 2 | Ex. 2 | Ex. 3 (reg. Ex. 2) |
|---|---|---|---|---|---|
| Mg [wt.-%] | 2.3 | 2.3 | 2.1 | 2.2 | n.a. |
| P [wt.-%] | — | — | 4.0 | 3.7 | n.a. |
| H₂O uptake [wt.-%] | 7.5 | 3.3 | 5.0 | 4.3 | n.a. |
| Selectivity [%]: | | | | | |
| ethylene | 6.0 | 5.9 | 6.2 | 6.0 | 3.8 |
| propylene | 42.4 | 42.6 | 38.7 | 37.8 | 39.5 |
| butylene | 24.6 | 27.3 | 25.0 | 24.6 | 22.5 |
| C₄ paraffins | 1.6 | 1.8 | 2.8 | 2.6 | 1.6 |
| C₅₊ (mixture) | 18.9 | 17.1 | 23.5 | 24.7 | 30.7 |
| aromatics | 4.3 | 3.8 | 2.4 | 2.9 | 1.1 |
| methane | 2.2 | 1.5 | 1.3 | 1.3 | 0.8 |
| Service life [h] | 100 | 249 | 192 | 307 | >250 |

As can be taken from the results displayed in Table 1, it has surprisingly been found that by reducing the water uptake in examples 1 and 2 compared to the catalysts according to comparative examples 1 and 2, the catalyst lifetime may be tremendously increased. More specifically, as may be taken from a comparison of Comparative Example 2 and Example 2, the increased hydrophobicity in Example 2 due to the reduced water uptake leads to an increase in lifetime of over 50%. In this respect it has quite unexpectedly been found that this may be achieved without noticeably influencing the catalyst selectivity, in particular relative to the conversion of diethylether to ethylene, propylene and butylene.

Comparison of Comparative Example 1 and Example 1 on the other hand, which as opposed to Comparative Example 2 and Example 2 do not contain phosphor, even more surprisingly reveals that an increase in hydrophobicity for the catalyst of Example 1 leads to an enormous increase in lifetime of about 150%. Thus, although the catalyst lifetime of Comparative Example 1 is much lower than for Comparative Example 2 containing phosphorous in addition to magnesium, the surface-treated catalyst sample of Example 1 displays an increase in catalyst lifetime which clearly surpasses the catalyst lifetime of the phosphorous containing catalyst of Comparative Example 2, and is only somewhat inferior to the catalyst lifetime a also been surface-treated for reduction of its water uptake, i.e. for increasing its hydrophobicity. Compared to the phosphorous containing samples, however, the selectivity of the samples according to Comparative Example 1 and Example 1 are higher relative to propylene compared to the catalyst samples of Comparative Example 2 and Example 2.

As concerns Example 1, however, it has quite surprisingly been found that as opposed to the phosphorous containing samples wherein the selectivities remain more or less unchanged, in particular relative to the production of ethylene, propylene, and butylene, the reduction of the water uptake in Example 1 actually leads to a notable increase in the selectivity towards butylene, while leaving the selectivities towards ethylene and propylene practically unchanged. Accordingly, with respect to the samples of Example 1 which does not contain phosphorous, it has quite unexpectedly found that not only may the catalyst lifetime be formidably increased by the reduction of the water uptake. Far more, the selectivity of the conversion of dimethylether to butylene may even be increased, while maintaining the high level of selectivity towards ethylene and propylene respectively achieved by the catalyst of Comparative Example 1 which has not been surface-treated for reducing the water uptake thereof.

Based on these unexpected effects which can be brought about by the surface-treatment for reducing the water uptake of a catalyst containing an alkaline earth metal and optionally further containing phosphorus and according to the present invention, a catalyst is thus provided for the conversion of oxygenates to olefins which, as has been shown by the test results in the DT3/4 process according to example 4, not only enables tremendously longer service lives, but also maintains a high selectivity towards $C_3$ and $C_4$ olefins compared to untreated samples. Furthermore, it has been unexpectedly found that in the absence of optional phosphorous, the selectivity towards $C_4$ may even be increased in addition to the considerable increase in catalyst lifetime while maintaining a high level of selectivity towards $C_3$ olefins compared to the untreated samples.

PRIOR ART DOCUMENTS

DD 238733 A1
McIntosh et al. in Applied Catalysis 1983, 6, p. 307-314
Lee et al. in Applied Catalysis A 2010, 374, p. 18-25
Freiding et al. in Applied Catalysis A 2007, 328, p. 210-218
U.S. Pat. No. 4,049,573
Goryainova et al. in Petroleum Chemistry 2011, vol. 51, no. 3, p. 169-173
Ciambelli et al. "Acid-base catalysis in the conversion of methanol to olefins over Mg-modified ZSM-5 zeolite", Successful Design of Catalysts, Elsevier Science Publishers B.V., Amsterdam, 1988, p. 239-246
Okado et al. in Applied Catalysis 1988, 41, p. 121-135
WO 2012/123556 A1
WO 2012/123557 A1
WO 2012/123558 A1
CN 102049302 A
CN 102049313 A
JP 2012-087079 A
US 006051519 A
WO 2012/152406 A1
WO 2011/089263
U.S. Pat. No. 4,504,690 A
Zhao et al. in Catalysis Today 2011, 160, pp. 179-183
Zhao et al. in Catalysis Today 2010, 156, pp. 69-73
Le Van Mao et al. in Can. J. Chem. 1985, 63, pp. 3464-3470

The invention claimed is:

1. A catalyst for the conversion of oxygenates to olefins, wherein the catalyst comprises one or more zeolites of the MFI, MEL and/or MWW structure type and particles of one or more metal oxides,
   the one or more zeolites of the MFI, MEL and/or MWW structure type comprising one or more alkaline earth metals selected from the group consisting of Mg, Ca, Sr, Ba and combinations thereof,
wherein the catalyst displays a water uptake of 9.0 wt.-% or less;
wherein the catalyst has been subjected to silylation with one or more silylating agent.

2. The catalyst of claim 1, wherein the particles of the one or more metal oxides comprise phosphorus, the phosphorus being present at least partly in oxidic form.

3. The catalyst of claim 1, wherein the one or more zeolites of the MFI, MEL and/or MWW structure type comprise phosphorus, the phosphorus being present at least partly in oxidic form.

4. The catalyst of claim 1, wherein the one or more zeolites are of the MFI structure type.

5. The catalyst of claim 1, wherein the alkaline earth metals are selected from the group consisting of Mg, Ca, Sr and combinations thereof.

6. The catalyst of claim 1, wherein the one or more zeolites of the MFI, MEL and/or MWW structure type comprise the one or more alkaline earth metals in a total amount in the range from 0.1 to 20% by weight, based on the total amount of the one or more zeolites of the MFI, MEL and/or MWW structure type and calculated as the metal.

7. The catalyst of claim 1, wherein the one or more metal oxides are selected from the group consisting of silica, alumina, titania, zirconia, aluminum-titanium mixed oxides, aluminum-zirconium mixed oxides, aluminum-lanthanum mixed oxides, aluminum-zirconium-lanthanum mixed oxides, titanium-zirconium mixed oxides and mixtures thereof.

8. The catalyst of claim 1, wherein the zeolite:metal oxide weight ratio in the catalyst is in the range from 10:90 to 95:5.

9. The catalyst of claim 2, wherein the total amount of phosphorus, based on the sum of the total weight of zeolites of the MFI, MEL and/or MWW structure type and the total weight of the particles of the one or more metal oxides and calculated as the element, is in the range from 0.1 to 20% by weight.

10. The catalyst of claim 1, wherein the catalyst is in the form of a shaped body comprising a mixture of the one or more zeolites of the MFI, MEL and/or MWW structure type and of the particles of the one or more metal oxides.

11. A process for preparing the catalyst according to claim 1, comprising
   (I) providing a catalyst comprising one or more zeolites of the MFI, MEL and/or MWW structure type and particles of one or more metal oxides, the one or more zeolites of the MFI, MEL and/or MWW structure type comprising one or more alkaline earth metals selected from the group consisting of Mg, Ca, Sr, Ba and combinations thereof;
   (II) treating the catalyst with one or more silylating agents; and
   (III) optionally calcining the silylated catalyst obtained in (II).

12. The process of claim 11, wherein step (I) comprises
   (I.a) providing one or more zeolites of the MFI, MEL and/or MWW structure type;
   (I.b) impregnating the one or more zeolites of the MFI, MEL and/or MWW structure type with a solution comprising the one or more alkaline earth metals;
   (I.c) optionally drying the one or more impregnated zeolites obtained in (I.b);
   (I.d) optionally calcining the one or more impregnated zeolites obtained in (I.b) or (I.c);
   (I.e) preparing a mixture comprising the one or more impregnated and optionally dried and/or calcined zeolites of the MFI, MEL and/or MWW structure type, one or more solvents and particles of the one or more metal oxides and/or precursor compounds of the one or more particles of the one or more metal oxides;
   (I.f) homogenizing the mixture obtained in (I.e);
   (I.g) extruding the homogenized mixture obtained in (II);
   (I.h) optionally drying the extrudate obtained in (I.g);
   (I.i) optionally calcining the extrudate obtained in (I.g) or (I.h).

13. The process of claim 12, wherein step (I.e) comprises
   (I.e.1) preparing a mixture comprising the one or more impregnated and optionally dried and/or calcined zeolites of the MFI, MEL and/or MWW structure type and particles of the one or more metal oxides and/or precursor compounds of the one or more particles of the one or more metal oxides;

(I.e.2) admixing the mixture obtained in (I.e.1) with a phosphorus-comprising solution;

(I.e.3) mixing the mixture obtained in (I.e.2) with one or more solvents.

14. The process of claim 12, wherein step (I) further comprises (I.j) impregnating the optionally dried and/or calcined extrudate with a phosphorus-comprising solution;

(I.k) optionally drying the impregnated extrudate obtained in (I.j);

(I.l) optionally calcining the extrudate obtained in (I.j) or (I.k).

15. The process of claim 12, wherein the impregnating in (I.b) or the drying in (I.c) or the calcining in (I.d) is followed by bringing the one or more impregnated zeolites of the MFI, MEL and/or MWW structure type to a particle size $D_{50}$ in the range from 5 to 1000 urn.

16. The process of claim 12, wherein the drying in (I.c), (I.h) and/or (I.k) is effected at a temperature in the range from 50 to 220° C.

17. The process of claim 11, wherein the calcining in (I.d), (I.i), (I.l) and/or (III) is effected at a temperature in the range from 300 to 850° C.

18. The process of claim 12, wherein the solution used in (I.b) and/or (I.j) or (I.e.2) and/or the mixture prepared in (I.e) or (I.e.3) comprises one or more solvents selected from the group consisting of alcohols, water, mixtures of two or more alcohols, and mixtures of water and one or more alcohols.

19. The process of claim 11, wherein the one or more silylating agents are selected from the group consisting of alkyldisilazanes, alkylalkoxysilanes, haloalkylsilanes, and mixtures thereof.

20. The process of claim 19, wherein the alkyldisilazanes are selected from the group consisting of hexaalkyldisilazanes.

21. The process of claim 19, wherein the alkylalkoxysilanes are selected from the group consisting of trialkylalkoxysilanes, alkyltrialkoxysilanes, and mixtures thereof.

22. The process of claim 19, wherein the haloalkylsilanes are selected from the group consisting of dihalodialkylsilanes, and wherein independently from one another the halo groups are selected from the group consisting of halogens and pseudohalogens.

23. The process of claim 11, wherein step (II) is conducted under heating.

24. A catalyst for the conversion of oxygenates to olefins, obtained by a process according to claim 11.

25. A process for converting oxygenates to olefins, comprising:

(1) providing a gas stream comprising one or more oxygenates;

(2) contacting the gas stream with the catalyst according to claim 1.

26. The process of claim 25, wherein the gas stream according to (1) comprises one or more oxygenates selected from the group consisting of aliphatic alcohols, ethers, carbonyl compounds and mixtures thereof.

27. The process of claim 25, wherein the content of oxygenates in the gas stream according to (1) is in the range from 5% to 100% by volume based on the total volume.

28. The process of claim 25, wherein the water content in the gas stream according to (1) is in the range from 5 to 60% by volume based on the total volume.

29. The process of claim 25, wherein the contacting according to (2) is effected at a temperature in the range from 200 to 700° C.

30. The process of claim 25, wherein the contacting according to (2) is effected at a pressure in the range from 0.1 to 10 bar.

31. The process of claim 25, wherein the process is a continuous process.

32. The process of claim 31, in which the space velocity in the contacting according to (2) is in the range from 0.5 to 50 $h^{-1}$.

33. The process of claim 32, in which the service life of the catalyst during which the continuous process is performed without interruption is in the range from 50 to 450 h.

* * * * *